US012635941B2

(12) United States Patent
Matsumoto et al.

(10) Patent No.: US 12,635,941 B2
(45) Date of Patent: May 26, 2026

(54) EXACERBATION PREDICTION DEVICE, COMPUTER PROGRAM, EXACERBATION PREDICTION METHOD, PREDICTION MODEL GENERATION METHOD, AND PREDICTION MODEL GENERATION DEVICE

(71) Applicant: TERUMO KABUSHIKI KAISHA, Tokyo (JP)

(72) Inventors: Shinsuke Matsumoto, Ashigarakami-gun (JP); Taiki Hayashi, Fujinomiya (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 18/606,073

(22) Filed: Mar. 15, 2024

(65) Prior Publication Data

US 2024/0306987 A1      Sep. 19, 2024

(30) Foreign Application Priority Data

Mar. 17, 2023     (JP) ................................. 2023-043427

(51) Int. Cl.
*G16H 50/20*     (2018.01)
*A61B 5/00*     (2006.01)
*G16H 10/60*     (2018.01)
*G16H 15/00*     (2018.01)

(52) U.S. Cl.
CPC .......... *A61B 5/4842* (2013.01); *A61B 5/7275* (2013.01); *G16H 10/60* (2018.01); *G16H 50/20* (2018.01)

(58) Field of Classification Search
CPC . A61B 5/4842; A61B 5/7275; A61B 5/02405; G16H 10/60; G16H 50/20; G16H 50/30
See application file for complete search history.

(56) References Cited

U.S. PATENT DOCUMENTS

| | | | |
|---|---|---|---|
| 11,832,928 B2 | 12/2023 | Kingsford | |
| 2021/0090694 A1* | 3/2021 | Colley | ................... G16B 30/00 |
| 2021/0257095 A1* | 8/2021 | Zacharia | ................ G06N 5/027 |
| 2021/0369394 A1* | 12/2021 | Braido | ................... G16H 20/40 |

FOREIGN PATENT DOCUMENTS

JP        2019509153 A      4/2019

OTHER PUBLICATIONS

U.S. Appl. No. 18/606,789, filed Maar. 15, 2024, Shinsuke Matsumoto et al.

* cited by examiner

*Primary Examiner* — Maroun P Kanaan
(74) *Attorney, Agent, or Firm* — .Buchanan Ingersoll & Rooney PC

(57)                ABSTRACT

An exacerbation prediction device that includes a control unit. The control unit is configured to acquire biological data of a target patient to be evaluated for exacerbation, measured by a device, specify feature amounts related to organ failure obtained by processing the acquired biological data, and input the biological data and the feature amounts to a prediction model for predicting exacerbation of a patient to predict exacerbation of the target patient.

11 Claims, 28 Drawing Sheets

*FIG. 2*

BIOLOGICAL DATA

| |
|---|
| EXTRACELLULAR MOISTURE RESISTANCE VALUE |
| HEART RATE |
| PULSE RATE |
| RESPIRATORY RATE |
| ACTIVITY AMOUNT |
| ⋮ |

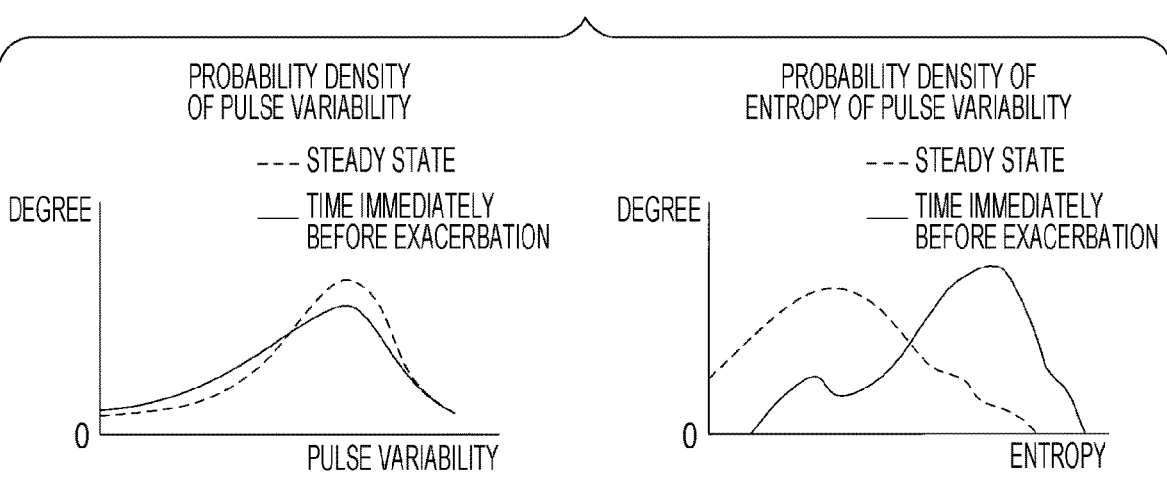

PROBABILITY DENSITY
OF PULSE VARIABILITY

- - - STEADY STATE
⎯ TIME IMMEDIATELY
BEFORE EXACERBATION

DEGREE

0    PULSE VARIABILITY

PROBABILITY DENSITY OF
ENTROPY OF PULSE VARIABILITY

- - - STEADY STATE
⎯ TIME IMMEDIATELY
BEFORE EXACERBATION

DEGREE

0    ENTROPY

FIG. 5B

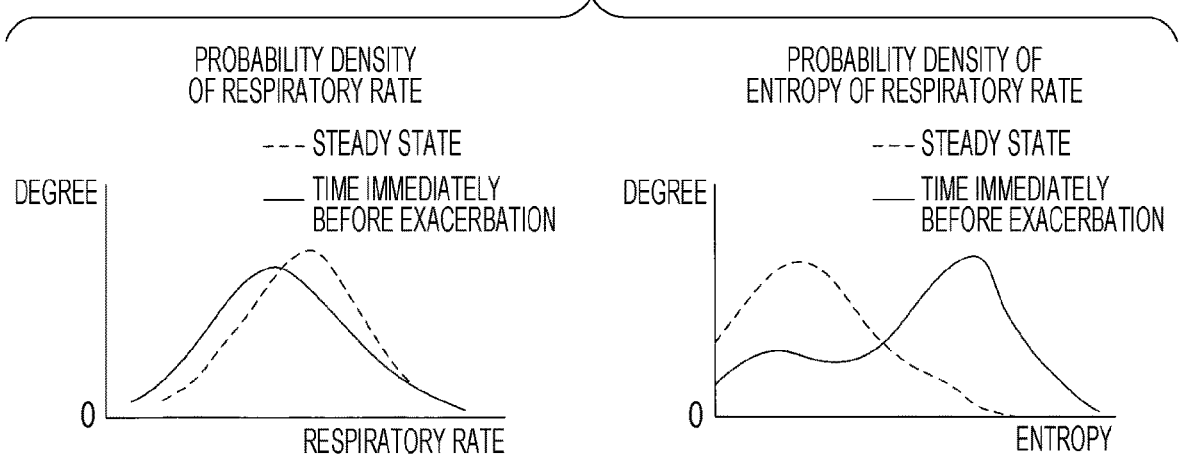

PROBABILITY DENSITY
OF RESPIRATORY RATE

- - - STEADY STATE
⎯ TIME IMMEDIATELY
BEFORE EXACERBATION

DEGREE

0    RESPIRATORY RATE

PROBABILITY DENSITY OF
ENTROPY OF RESPIRATORY RATE

- - - STEADY STATE
⎯ TIME IMMEDIATELY
BEFORE EXACERBATION

DEGREE

0    ENTROPY

*FIG. 6*

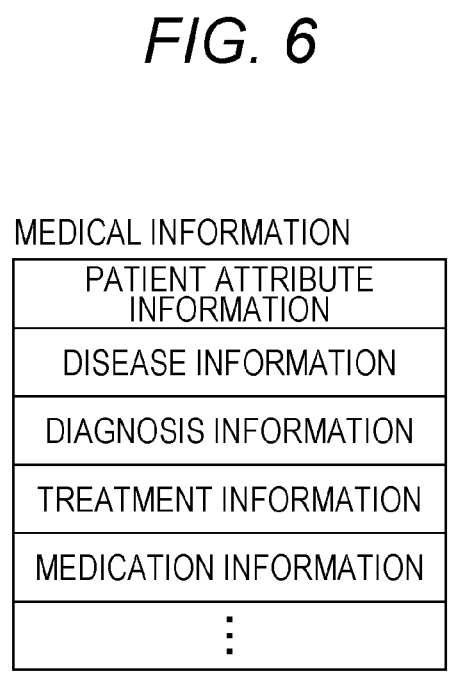

MEDICAL INFORMATION

| PATIENT ATTRIBUTE INFORMATION |
|---|
| DISEASE INFORMATION |
| DIAGNOSIS INFORMATION |
| TREATMENT INFORMATION |
| MEDICATION INFORMATION |
| ⋮ |

*FIG. 8*

PATIENT DB

| PATIENT ID | PATIENT ATTRIBUTE INFORMATION | BIOLOGICAL DATA HISTORY | FEATURE AMOUNT HISTORY | DISEASE HISTORY | DIAGNOSIS HISTORY | TREATMENT HISTORY | MEDICATION HISTORY |
|---|---|---|---|---|---|---|---|
| ID0001 | ×××| ×××| ×××| ×××| ×××| ×××| ×××|
| ID0002 | ○○○| ○○○| ○○○| ○○○| ○○○| ○○○| ○○○|
| ... | ... | ... | ... | ... | ... | ... | ... |

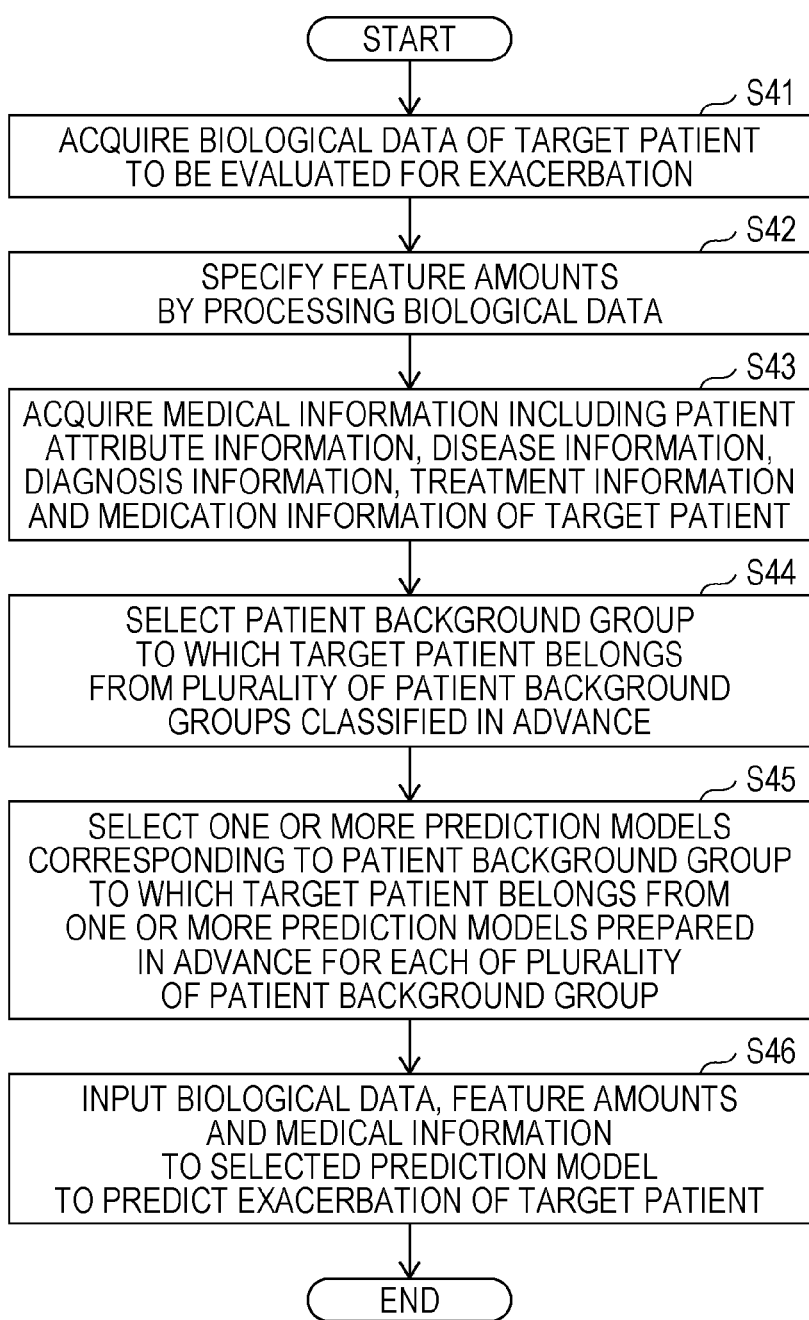

START

S41

ACQUIRE BIOLOGICAL DATA OF TARGET PATIENT
TO BE EVALUATED FOR EXACERBATION

S42

SPECIFY FEATURE AMOUNTS
BY PROCESSING BIOLOGICAL DATA

S43

ACQUIRE MEDICAL INFORMATION INCLUDING PATIENT
ATTRIBUTE INFORMATION, DISEASE INFORMATION,
DIAGNOSIS INFORMATION, TREATMENT INFORMATION
AND MEDICATION INFORMATION OF TARGET PATIENT

S44

SELECT PATIENT BACKGROUND GROUP
TO WHICH TARGET PATIENT BELONGS
FROM PLURALITY OF PATIENT BACKGROUND
GROUPS CLASSIFIED IN ADVANCE

S45

SELECT ONE OR MORE PREDICTION MODELS
CORRESPONDING TO PATIENT BACKGROUND GROUP
TO WHICH TARGET PATIENT BELONGS FROM
ONE OR MORE PREDICTION MODELS PREPARED
IN ADVANCE FOR EACH OF PLURALITY
OF PATIENT BACKGROUND GROUP

S46

INPUT BIOLOGICAL DATA, FEATURE AMOUNTS
AND MEDICAL INFORMATION
TO SELECTED PREDICTION MODEL
TO PREDICT EXACERBATION OF TARGET PATIENT

END

FIG. 14

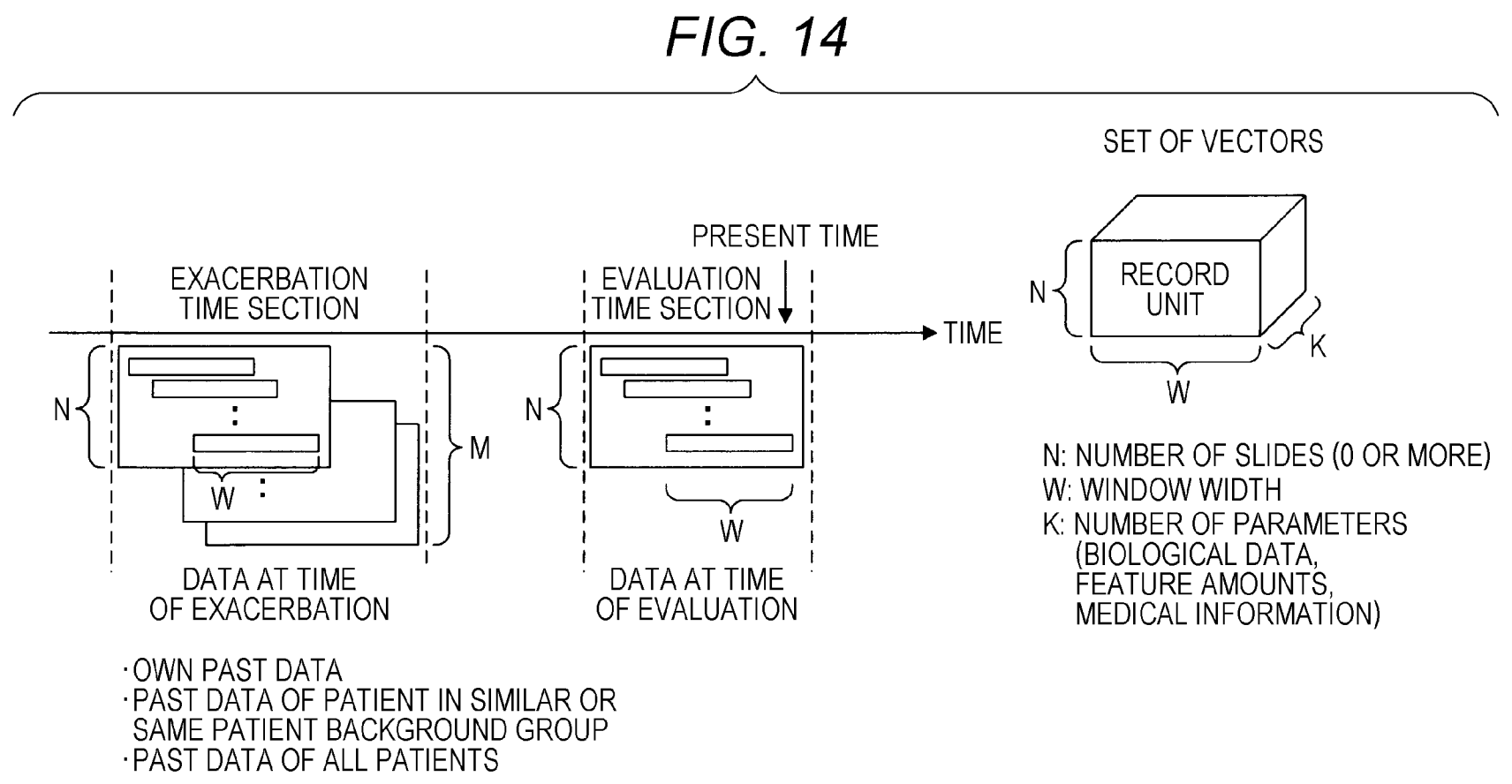

SET OF VECTORS

RECORD UNIT

N
W
K

N: NUMBER OF SLIDES (0 OR MORE)
W: WINDOW WIDTH
K: NUMBER OF PARAMETERS
(BIOLOGICAL DATA,
FEATURE AMOUNTS,
MEDICAL INFORMATION)

TIME

PRESENT TIME

EVALUATION TIME SECTION

W

DATA AT TIME OF EVALUATION

N

EXACERBATION TIME SECTION

M

W

DATA AT TIME OF EXACERBATION

N

·OWN PAST DATA
·PAST DATA OF PATIENT IN SIMILAR OR
 SAME PATIENT BACKGROUND GROUP
·PAST DATA OF ALL PATIENTS

FIG. 19A
TRAINING INPUT DATA                              TEACHER LABEL
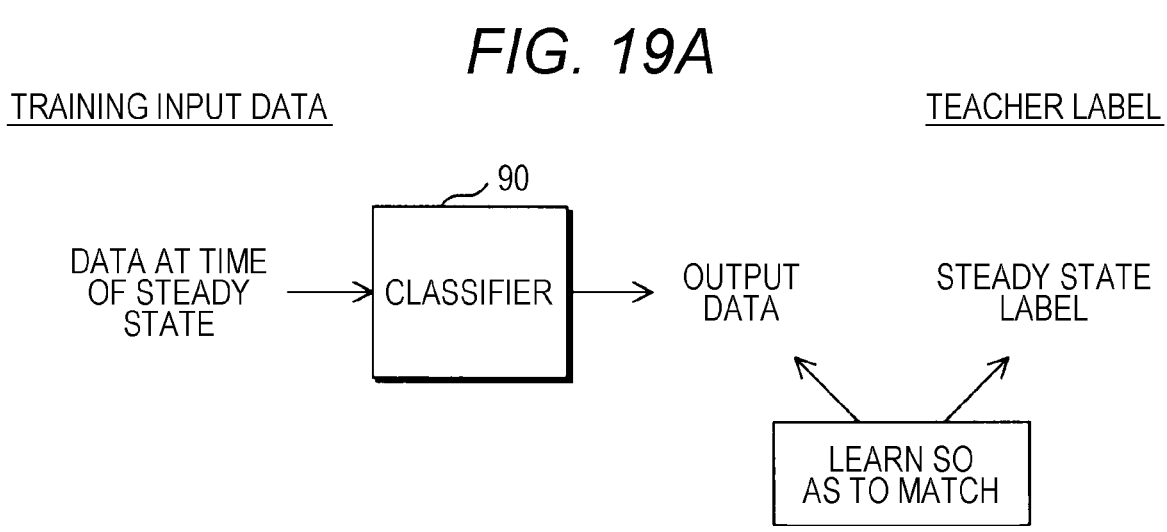
FIG. 19B
TRAINING INPUT DATA                              TEACHER LABEL
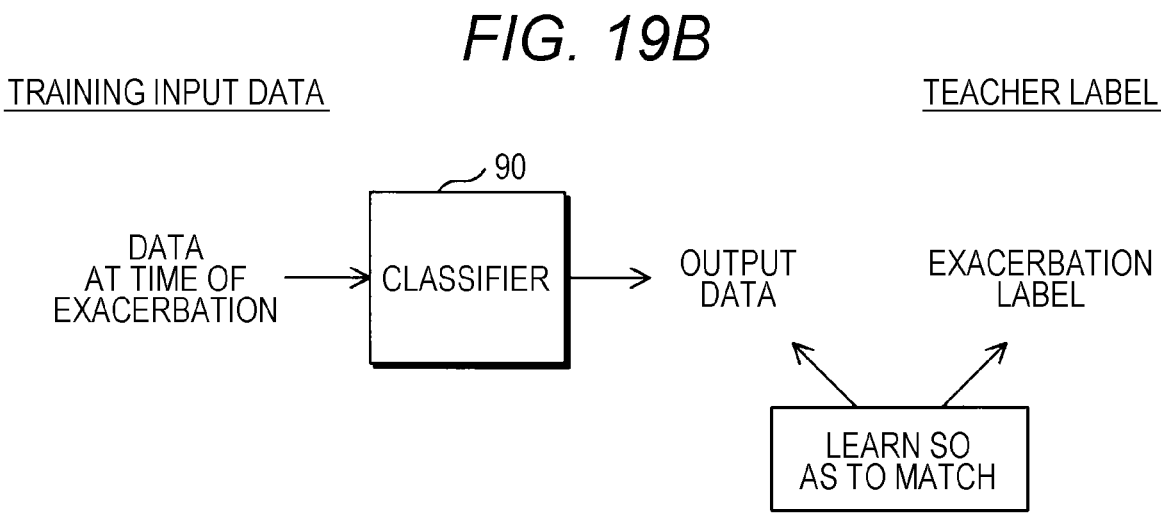
FIG. 19C
DATA
AT TIME OF
EVALUATION  →  CLASSIFIER  ⟶○ STEADY STATE (PROBABILITY)
90
⟶○ EXACERBATION (PROBABILITY)

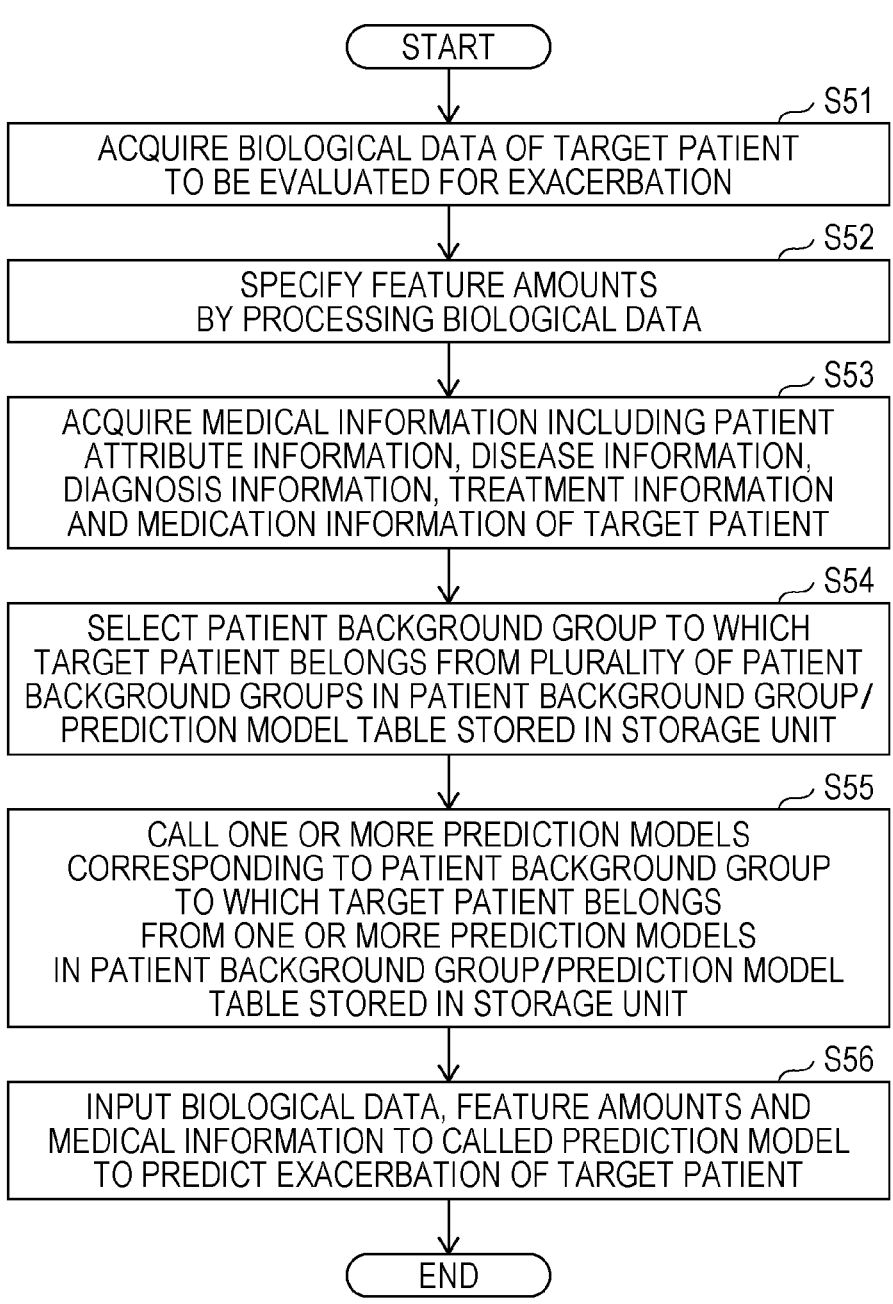

START

↓ S51

ACQUIRE BIOLOGICAL DATA OF TARGET PATIENT
TO BE EVALUATED FOR EXACERBATION

↓ S52

SPECIFY FEATURE AMOUNTS
BY PROCESSING BIOLOGICAL DATA

↓ S53

ACQUIRE MEDICAL INFORMATION INCLUDING PATIENT
ATTRIBUTE INFORMATION, DISEASE INFORMATION,
DIAGNOSIS INFORMATION, TREATMENT INFORMATION
AND MEDICATION INFORMATION OF TARGET PATIENT

↓ S54

SELECT PATIENT BACKGROUND GROUP TO WHICH
TARGET PATIENT BELONGS FROM PLURALITY OF PATIENT
BACKGROUND GROUPS IN PATIENT BACKGROUND GROUP/
PREDICTION MODEL TABLE STORED IN STORAGE UNIT

↓ S55

CALL ONE OR MORE PREDICTION MODELS
CORRESPONDING TO PATIENT BACKGROUND GROUP
TO WHICH TARGET PATIENT BELONGS
FROM ONE OR MORE PREDICTION MODELS
IN PATIENT BACKGROUND GROUP/PREDICTION MODEL
TABLE STORED IN STORAGE UNIT

↓ S56

INPUT BIOLOGICAL DATA, FEATURE AMOUNTS AND
MEDICAL INFORMATION TO CALLED PREDICTION MODEL
TO PREDICT EXACERBATION OF TARGET PATIENT

↓

END

EXACERBATION PREDICTION DEVICE, COMPUTER PROGRAM, EXACERBATION PREDICTION METHOD, PREDICTION MODEL GENERATION METHOD, AND PREDICTION MODEL GENERATION DEVICE

CROSS-REFERENCES TO RELATED APPLICATIONS

This application claims priority to Japanese Application No. 2023-043427 filed on Mar. 17, 2023, the entire content of which is incorporated herein by reference.

TECHNOLOGICAL FIELD

The present disclosure generally relates to an exacerbation prediction device, a computer program, an exacerbation prediction method, a prediction model generation method, and a prediction model generation device.

BACKGROUND DISCUSSION

Organ failure such as circulatory failure is one of the main causes of death and the need for care. It is important to grasp an actual state of medical care such as a condition of a patient and treatment details in order to take measures against organ failure. In addition, the number of patients with organ failure is increasing, and thus, it is important to detect exacerbation of a patient at a timing as early as possible to help prevent re-hospitalization.

Japanese Patent Application Publication No. 2019-509153 A discloses a technique for determining a first body fluid level indicator and a second body fluid level indicator on the basis of a first impedance and a second impedance, respectively measured from a sensor electrically connected to a subject, determining a body fluid level change on the basis of a difference between the first body fluid level indicator and the second body fluid level indicator, and determining a heart failure indicator using the determined body fluid level change.

In the technique of Japanese Patent Application Publication No. 2019-509153 A, heart failure is detected using a body fluid level, but in order to detect organ failure, it is necessary to confirm various pieces of biological information of a patient, and it can be difficult for an unskilled medical worker to make a judgment. The number of skilled doctors for an organ failure patient is not sufficient. In addition, patient background varies for each patient, and biological information of the patient changes according to the patient background, so that it can be difficult to accurately determine exacerbation.

SUMMARY

An exacerbation prediction device, a computer program, an exacerbation prediction method, a prediction model generation method, and a prediction model generation device capable of improving accuracy of prediction of exacerbation of an organ failure patient.

(1) An exacerbation prediction device according to the present disclosure includes a control unit, in which the control unit is configured to acquire biological data of a target patient to be evaluated for exacerbation, measured by a device, specify feature amounts related to organ failure obtained by processing the acquired biological data, and input the acquired biological data and the specified feature amounts to a prediction model for predicting exacerbation of a patient to predict exacerbation of the target patient.

(2) In the exacerbation prediction device of (1), the control unit is configured to acquire medical information depending on at least one of patient attribute information, disease information, diagnosis information, treatment information, or medication information of the target patient and input the medical information to the prediction model to predict exacerbation of the target patient.

(3) In the exacerbation prediction device of (1) or (2), the control unit is configured to select a patient background group to which the target patient belongs, from a plurality of patient background groups classified in advance on the basis of the biological data and the feature amounts, select one or more prediction models corresponding to the patient background group to which the target patient belongs, from one or more prediction models prepared in advance for each of the plurality of patient background groups, and input the biological data and the feature amounts to the selected prediction model to predict exacerbation of the target patient.

(4) In the exacerbation prediction device according to any one of (1) to (3), the feature amounts include a temporal change feature amount that captures a temporal change in a state of the target patient based on time-series data obtained within a predetermined period of the biological data.

(5) In the exacerbation prediction device according to any one of (1) to (4), the temporal change feature amount includes at least one of a blood pressure change index, heart rate variability, pulse variability, a respiration complexity, or a complexity of the heart rate variability.

(6) In the exacerbation prediction device according to any one of (1) to (5), the temporal change feature amount includes at least one of changes in periodicity of a residual component and a trend component separated from tendency target information including at least one of the biological data or the feature amounts obtained by processing the biological data, and a seasonal periodic component separated from the tendency target information.

(7) In the exacerbation prediction device according to any one of (1) to (6), the temporal change feature amount includes probability density of entropy of at least one of the biological data or the feature amounts obtained by processing the biological data.

(8) A non-transitory computer-readable program storing a computer program according to the present disclosure causes a computer to execute a process comprising: acquiring biological data of a target patient to be evaluated for exacerbation measured by a device, specifying feature amounts related to organ failure obtained by processing the acquired biological data, and inputting the biological data and the feature amounts to a prediction model for predicting exacerbation of a patient to predict exacerbation of the target patient.

(9) An exacerbation prediction method according to the present disclosure includes acquiring biological data of a target patient to be evaluated for exacerbation, measured by a device, specifying feature amounts related to organ failure obtained by processing the acquired biological data and inputting the biological data and the feature amounts to a prediction model for predicting exacerbation of a patient to predict exacerbation of the target patient.

(10) A prediction model generation method according to the present disclosure includes acquiring biological data of a patient, specifying feature amounts related to organ failure obtained by processing the acquired biological data, and generating a prediction model so as to predict exacerbation of the patient in a case where the biological data and the feature amounts are input, on the basis of training data including the biological data and the feature amounts.

(11) A prediction model generation device according to the present disclosure includes a control unit, in which the control unit is configured to acquire biological data of a patient, specify feature amounts related to organ failure obtained by processing the acquired biological data, and generate a prediction model so as to predict exacerbation of the patient in a case where the biological data and the feature amounts are input, on the basis of training data including the biological data and the feature amounts.

(12) A non-transitory computer-readable medium storing a computer program according to the present disclosure that causes a computer to execute processing of acquiring biological data of a patient, specifying feature amounts related to organ failure obtained by processing the acquired biological data, and generating a prediction model so as to predict exacerbation of the patient in a case where the biological data and the feature amounts are input, on the basis of training data including the biological data and the feature amounts.

According to the present disclosure, accuracy of prediction of exacerbation of a patient with organ failure can be improved.

BRIEF DESCRIPTION OF THE DRAWINGS

FIG. 2 is a view illustrating an example of biological data to be measured by a wearable device.

FIG. 3 is a view illustrating an example of feature amounts related to organ failure.

FIGS. 5A and 5B are views illustrating an example of probability density of biological data and features amounts and probability density of entropy of biological data and feature amounts.

FIG. 6 is a view illustrating an example of medical information.

FIG. 8 is a view illustrating an example of a configuration of a patient database (DB).

FIG. 11 is a view illustrating an example of a patient background group/prediction model table.

FIG. 12 is a view illustrating a first example of prediction model execution processing.

FIG. 14 is a view illustrating a second example of creation of learning data;

4

Figure 18:
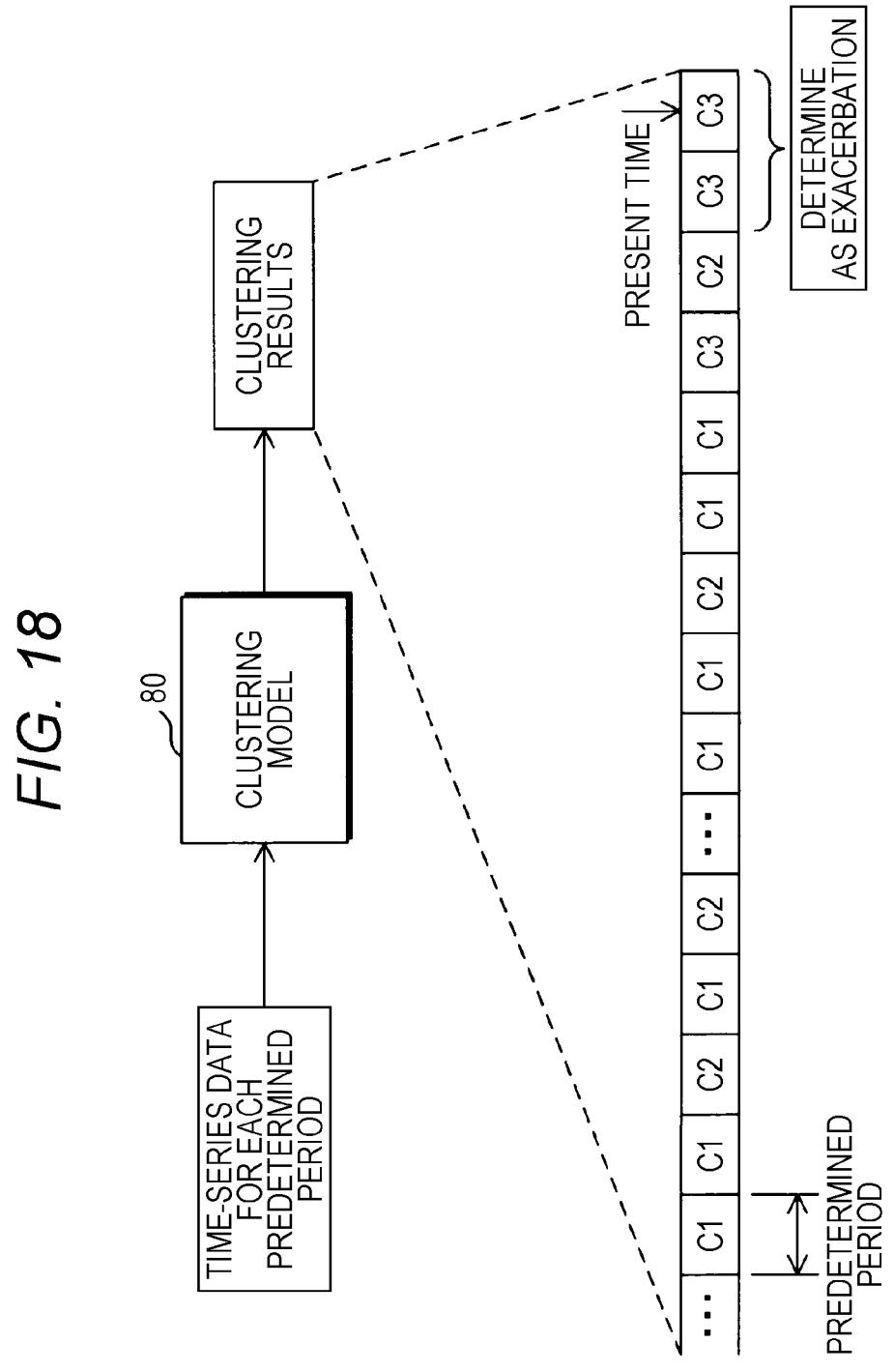

FIG. 18 is a view illustrating a second example of the clustering scheme.

FIGS. 19A to 19C are views illustrating an example of a classifier.

Figure 20:
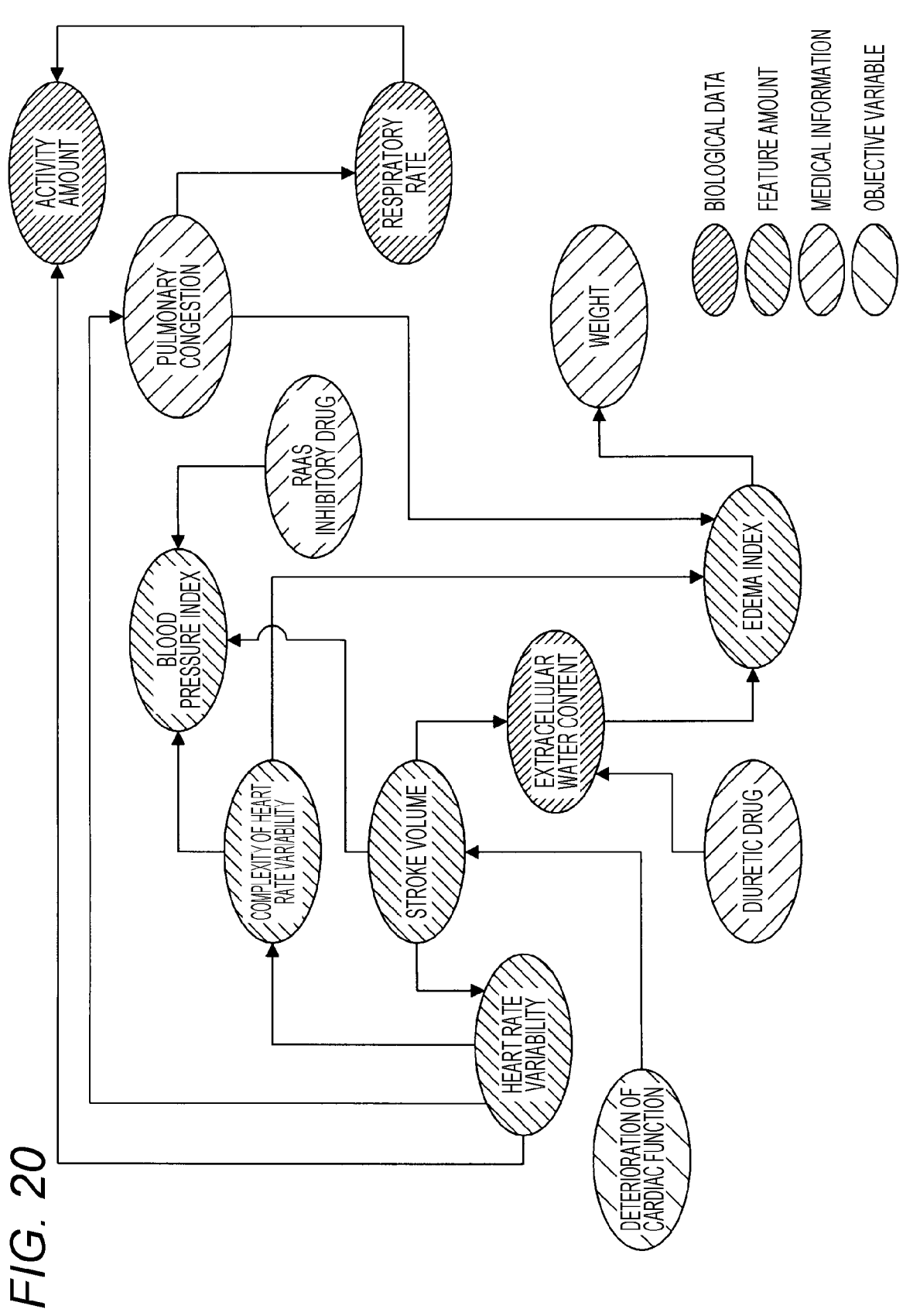

FIG. 20 is a view illustrating an example of a causal network model.

Figure 21:
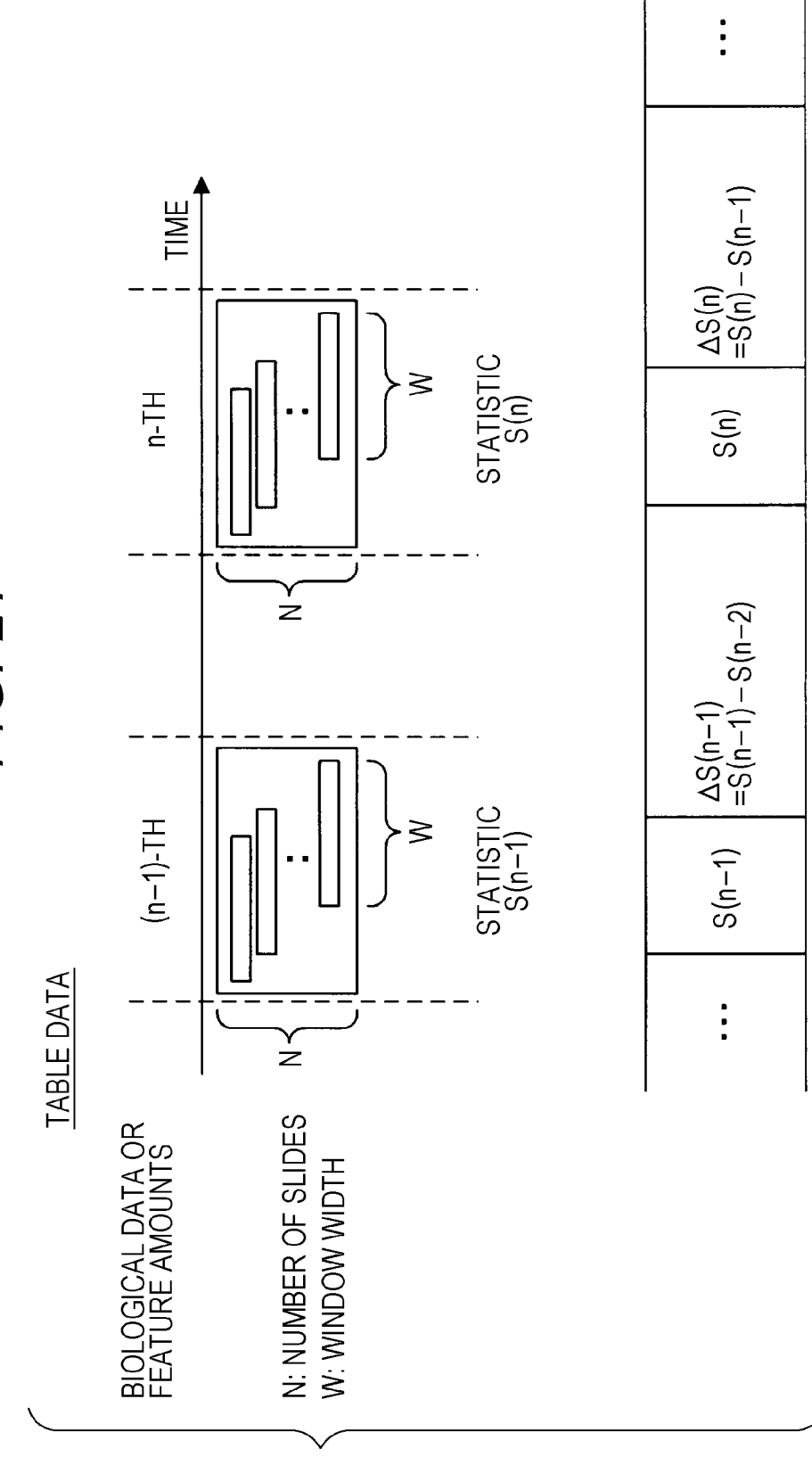

FIG. 21 is an example of a data table for giving biological data and a feature amount to a node.

Figure 22:
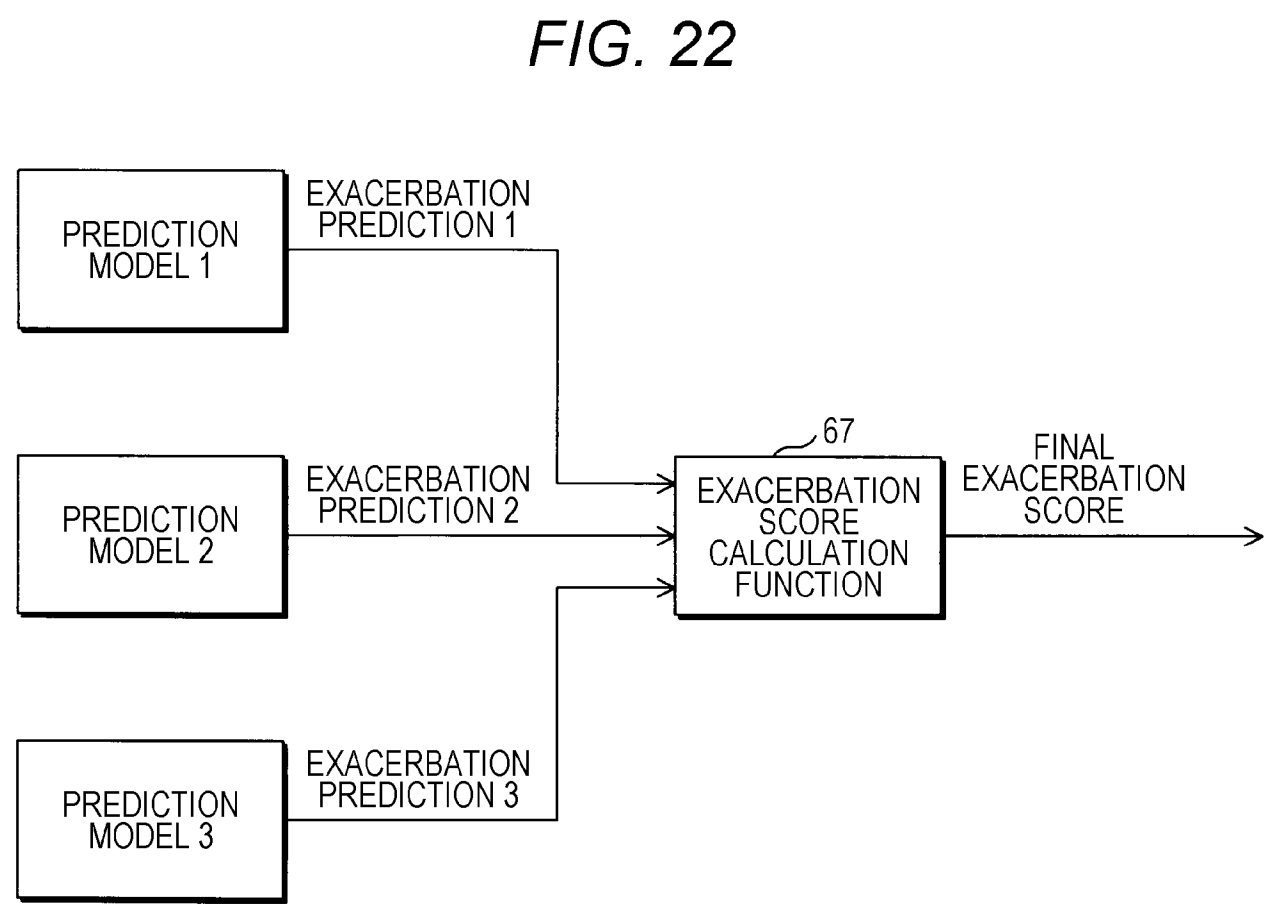

FIG. 22 is a view illustrating an example of calculation of an exacerbation score.

Figure 23:
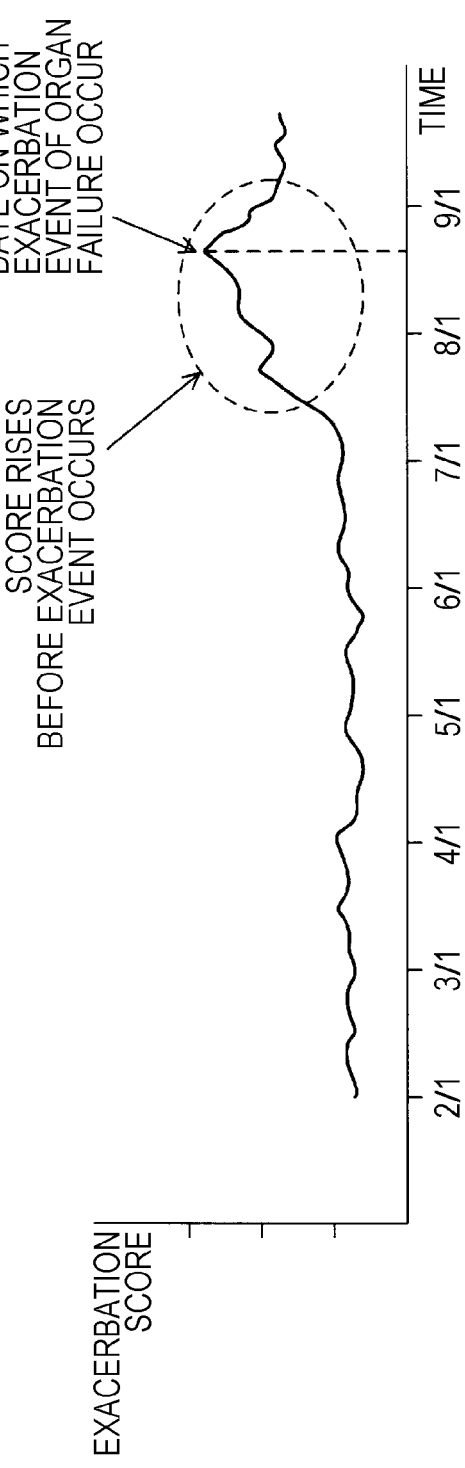

FIG. 23 is a view illustrating a first example of provision of exacerbation information.

Figure 24:
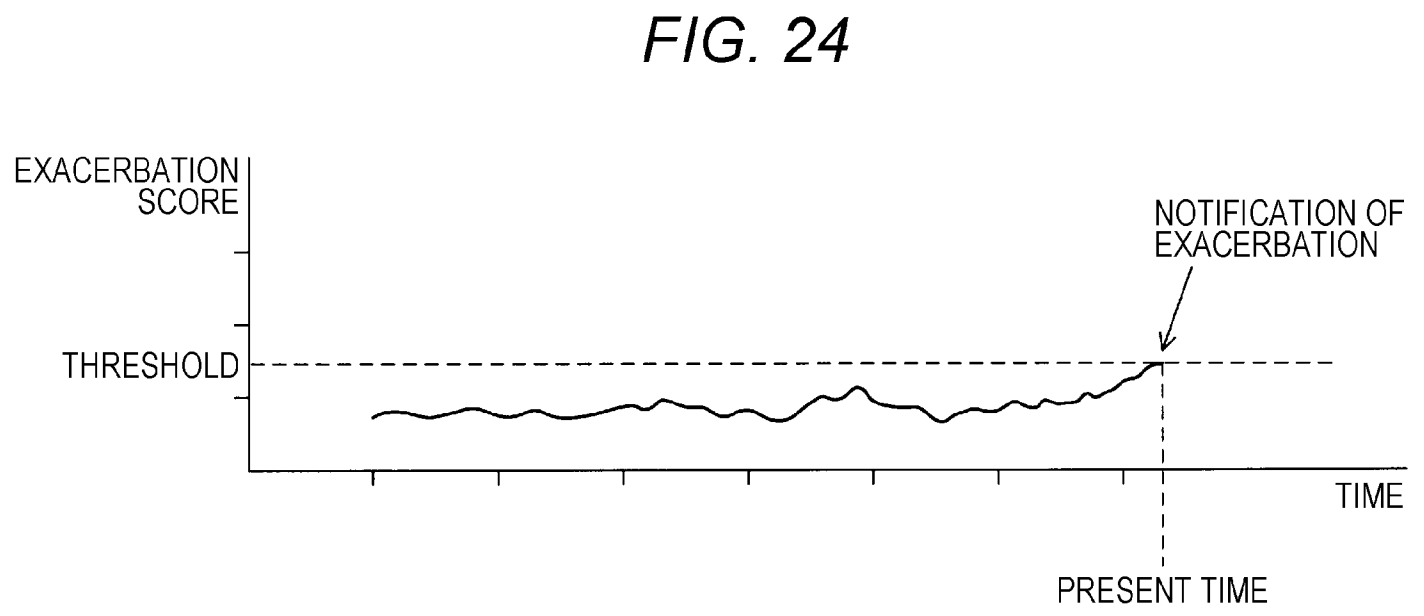

FIG. 24 is a view illustrating a second example of provision of exacerbation information.

Figure 25:
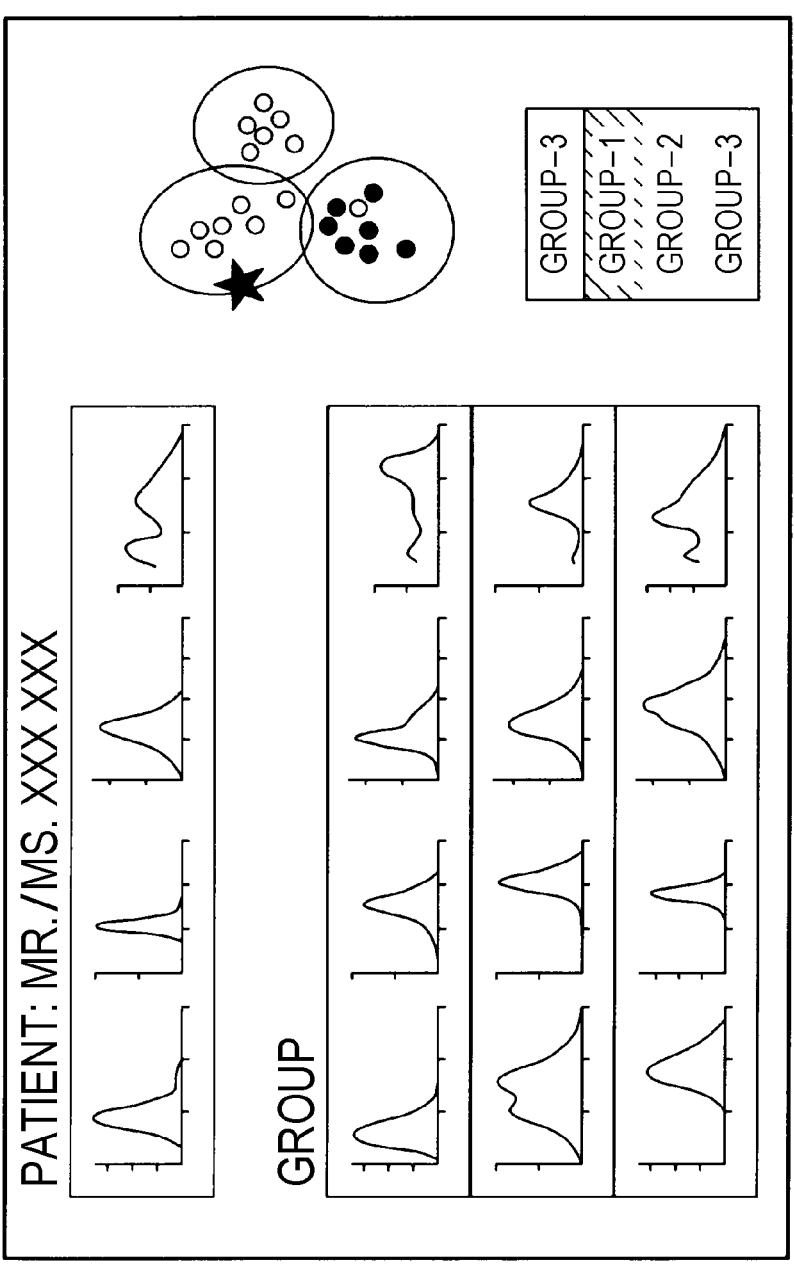

FIG. 25 is a view illustrating a third example of provision of exacerbation information.

Figure 26:
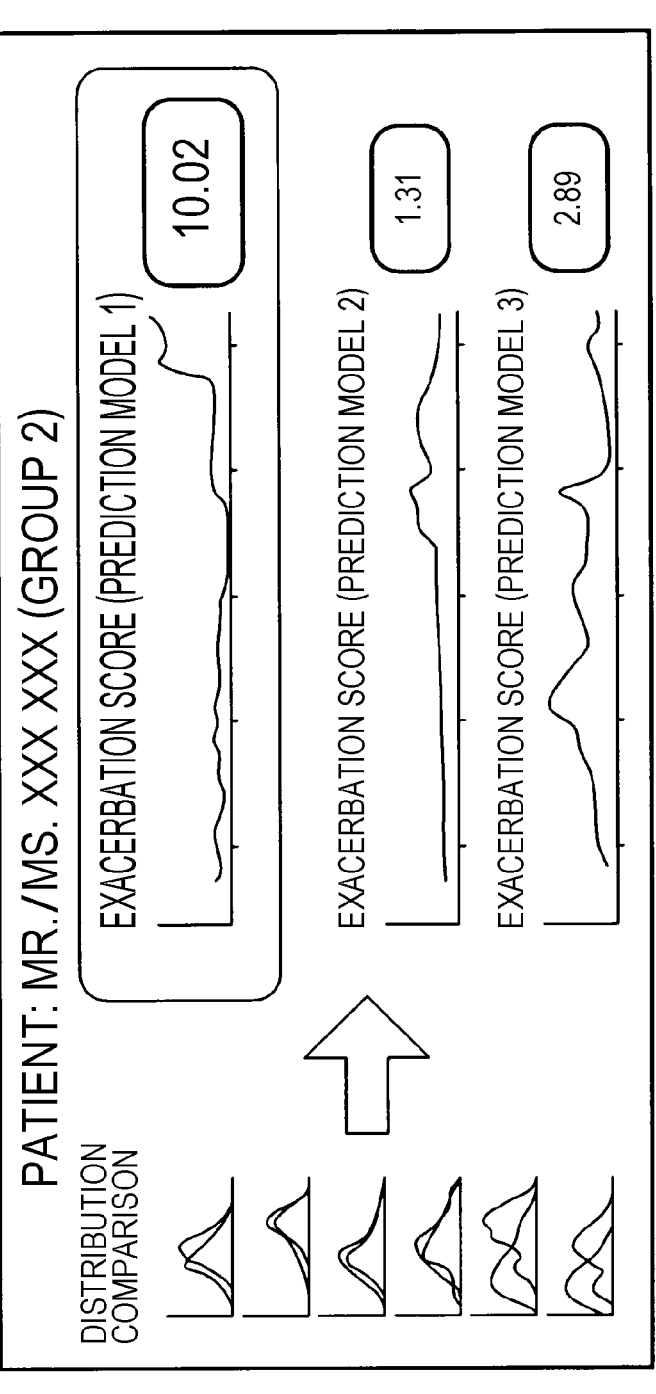

FIG. 26 is a view illustrating a fourth example of provision of exacerbation information.

Figure 27:
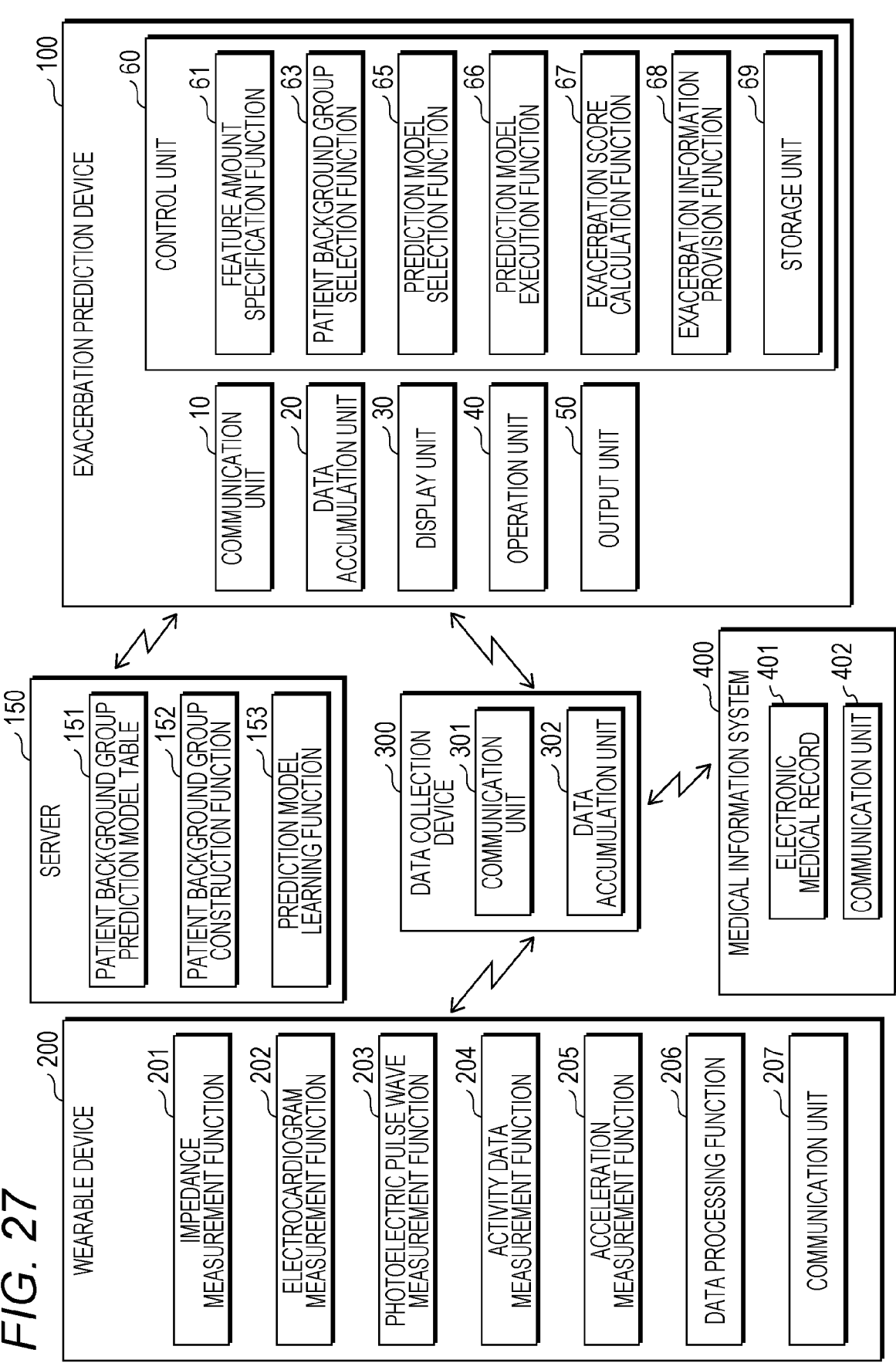

FIG. 27 is a view illustrating a second example of the configuration of the exacerbation prediction system of the present embodiment.

FIG. 28 is a view illustrating a second example of the prediction model execution processing.

DETAILED DESCRIPTION

Set forth below with reference to the accompanying drawings is a detailed description of embodiments of an exacerbation prediction device, a computer program, an exacerbation prediction method, a prediction model generation method, and a prediction model generation device capable of improving accuracy of prediction of exacerbation of an organ failure patient.

Figure 1:
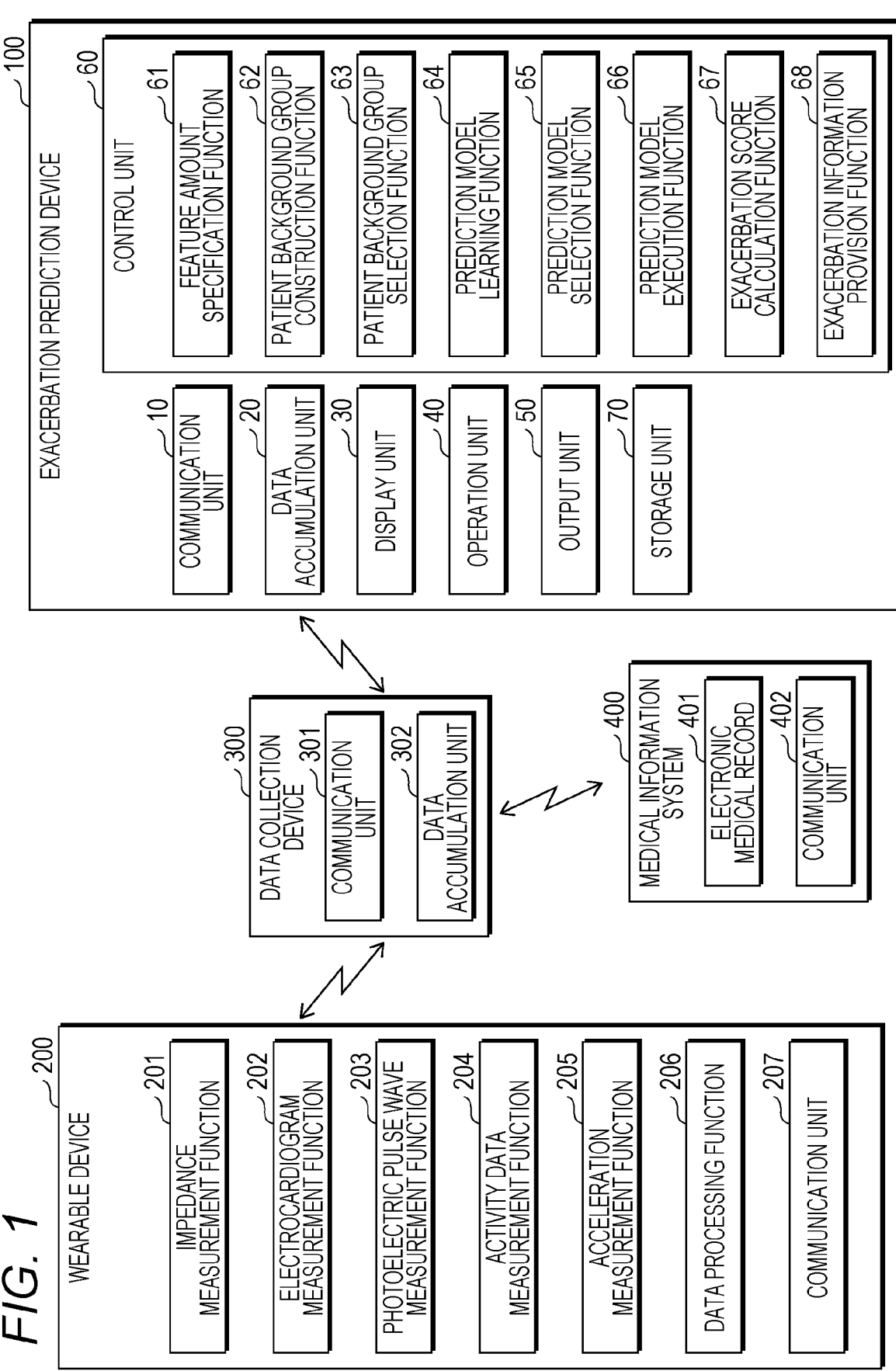
FIG. 1 is a view illustrating a first example of a configuration of an exacerbation prediction system of the present embodiment.

FIG. 1 is a view illustrating a first example of a configuration of an exacerbation prediction system of the present embodiment. The exacerbation prediction system of the present embodiment includes an exacerbation prediction device 100 and a data collection device 300. The exacerbation prediction system may include a wearable device 200 to be worn on a target patient to be evaluated for exacerbation and a medical information system 400. The exacerbation prediction device 100, the wearable device 200, and the medical information system 400 are connected to the data collection device 300 via a communication network. The exacerbation prediction device 100 can acquire biological data of the target patient from the wearable device 200 and medical information from the medical information system 400 via the data collection device 300.

The wearable device 200 is also referred to as a device and can include an impedance measurement function 201, an electrocardiogram measurement function 202, a photoelectric plethysmography function 203, an activity data measurement function 204, an acceleration measurement function 205, a data processing function 206, and a communication unit 207. The wearable device 200 measures biological data of the target patient and transmits the measured biological data to the data collection device 300.

FIG. 2 is a view illustrating an example of biological data to be measured by the wearable device 200. The biological data can include an extracellular water resistance value to be measured by the impedance measurement function 201, an electrocardiogram waveform or a heart rate to be measured by the electrocardiogram measurement function 202, a pulse wave or a pulse rate to be measured by the photoelectric plethysmography function 203, a respiratory rate to be measured by the electrocardiogram measurement function 202 or the acceleration measurement function 205, an activity amount to be measured by the activity data measurement function 204 or the acceleration measurement function 205, and the like. The wearable device 200 may be a device capable of measuring all or part of the biological data illustrated in FIG. 2. Note that the biological data is not limited to the data illustrated in FIG. 2.

The data processing function 206 attaches an identifier (ID) of the target patient to the measured biological data and outputs the biological data to the communication unit 207. The data processing function 206 may include a memory that temporarily stores the measured biological data.

Furthermore, the data processing function 206 can remove noise caused by a wearing state becoming unstable due to movement of the body of the patient who wears the wearable device 200 by using measured data such as acceleration, thereby deleting a section other than a reliability section of the measured data (section in which noise is equal to or less than an allowable value). Furthermore, the data processing function 206 may remove noise using peripheral data by a 3 sigma filter, a Hampel filter, or the like. Furthermore, the data processing function 206 may interpolate a section that has not been measured or a section from which noise has been removed through interpolation, linear interpolation, spline interpolation, or the like, using previous data.

The communication unit 207 transmits the biological data measured by the wearable device 200 and the identifier of the target patient to the data collection device 300. Although only one wearable device 200 is illustrated in the example of FIG. 1, there may be a plurality of wearable devices 200 for the respective target patients.

The data collection device 300 includes a communication unit 301 and a data accumulation unit 302. The data collection device 300 classifies and collects the biological data measured by the wearable device 200 for each target patient. In addition, the data collection device 300 collects the medical information transmitted by the medical information system 400. In this case, in a case where the medical information is information that can be classified for each target patient, the data collection device 300 classifies and collects the medical information for each target patient.

The medical information system 400 can include an electronic medical record 401, a communication unit 402, and the like. In the electronic medical record 401, medical information on not only the target patient to be evaluated for exacerbation but also all organ failure patients is recorded. The medical information recorded in the electronic medical record 401 is transmitted to the data collection device 300 via the communication unit 402.

The data accumulation unit 302 collects the biological data measured by the wearable device 200 and the medical information transmitted by the medical information system 400.

The communication unit 301 implements a communication function with the wearable device 200, the exacerbation prediction device 100, and the medical information system 400. The communication unit 301 transmits the biological data and the medical information accumulated in the data accumulation unit 302 to the exacerbation prediction device 100.

The exacerbation prediction device 100 includes a communication unit 10, a data accumulation unit 20, a display unit 30, an operation unit 40, an output unit 50, a storage unit 70, and a control unit 60.

The communication unit 10 implements a communication function with the data collection device 300. The communication unit 10 receives the biological data and the medical information transmitted by the data collection device 300.

The data accumulation unit 20 collects the biological data and the medical information transmitted by the data collection device 300.

The display unit 30 can include a liquid crystal panel, an organic electro luminescence (EL) display, or the like. The display unit 30 displays a processing result (for example, an exacerbation determination result, or the like) of the exacerbation prediction device 100. An external display device (for example, a personal computer, or the like, to be used by a medical worker) may be provided instead of the display unit 30, and the processing result of the exacerbation prediction device 100 may be displayed on the display device, for example, using a web application.

The operation unit 40 can include, for example, a keyboard, a mouse, and the like, and can operate an icon, and the like, displayed on the display unit 30, move and operate a cursor, input characters, and the like. The operation unit 40 may include a touch panel.

The output unit 50 outputs the processing result (for example, an exacerbation determination result, or the like) of the exacerbation prediction device 100 to another device.

The storage unit 70 includes a hard disk, a semiconductor memory, or the like, and can store a plurality of patient background groups obtained by classifying a plurality of patients collected in advance by patient data, and one or more prediction models prepared in advance for each of the plurality of patient background groups. The storage unit 70 can store these patient background groups and prediction models in the form of a patient background group/prediction model table illustrated in FIG. 11.

The control unit 60 may be configured by incorporating a required number of central processing units (CPUs), microprocessing units (MPUs), graphics processing units (GPUs), and the like. Furthermore, the control unit 60 may be configured by combining digital signal processors (DSPs), field-programmable gate arrays (FPGAs), and the like. The control unit 60 includes a semiconductor memory such as a flash memory and stores a computer program (program product). The control unit 60 can execute a computer program loaded in a semiconductor memory. The computer program may be downloaded from an external device via the communication unit 10 and stored in the semiconductor memory. In addition, a computer program recorded on a recording medium (for example, an optically readable disk storage medium such as a CD-ROM) may be read by a recording medium reading unit and stored in the semiconductor memory. The computer program may be stored in a storage unit of the hard disk. The computer program can be loaded so as to be executed on a single computer or on a plurality of computers which are located at one site or distributed across a plurality of sites and interconnected by a communication network.

The control unit 60 includes a feature amount specification function 61, a patient background group construction function 62, a patient background group selection function 63, a prediction model learning function 64, a prediction model selection function 65, a prediction model execution function 66, an exacerbation score calculation function 67, and an exacerbation information provision function 68. Note that, in a case where the exacerbation prediction device 100 is a device that executes a learned prediction model and is a device that does not perform relearning, the patient background group construction function 62 and the prediction model learning function 64 are not essential configurations.

The prediction model execution function 66 and the exacerbation score calculation function 67 collectively function as a prediction unit.

The control unit 60 has a function as a patient data acquisition unit and acquires biological data of the target patient to be evaluated for exacerbation measured by the wearable device 200 from the data accumulation unit 20.

The feature amount specification function 61 specifies feature amounts related to organ failure obtained by processing the acquired biological data. The organ failure can include, for example, a circulatory failure, and the circulatory failure includes heart failure, renal failure, and the like. The control unit 60 has a function as a patient data acquisition unit and acquires the feature amounts of the target patient specified by the feature amount specification function 61.

Figure 3:
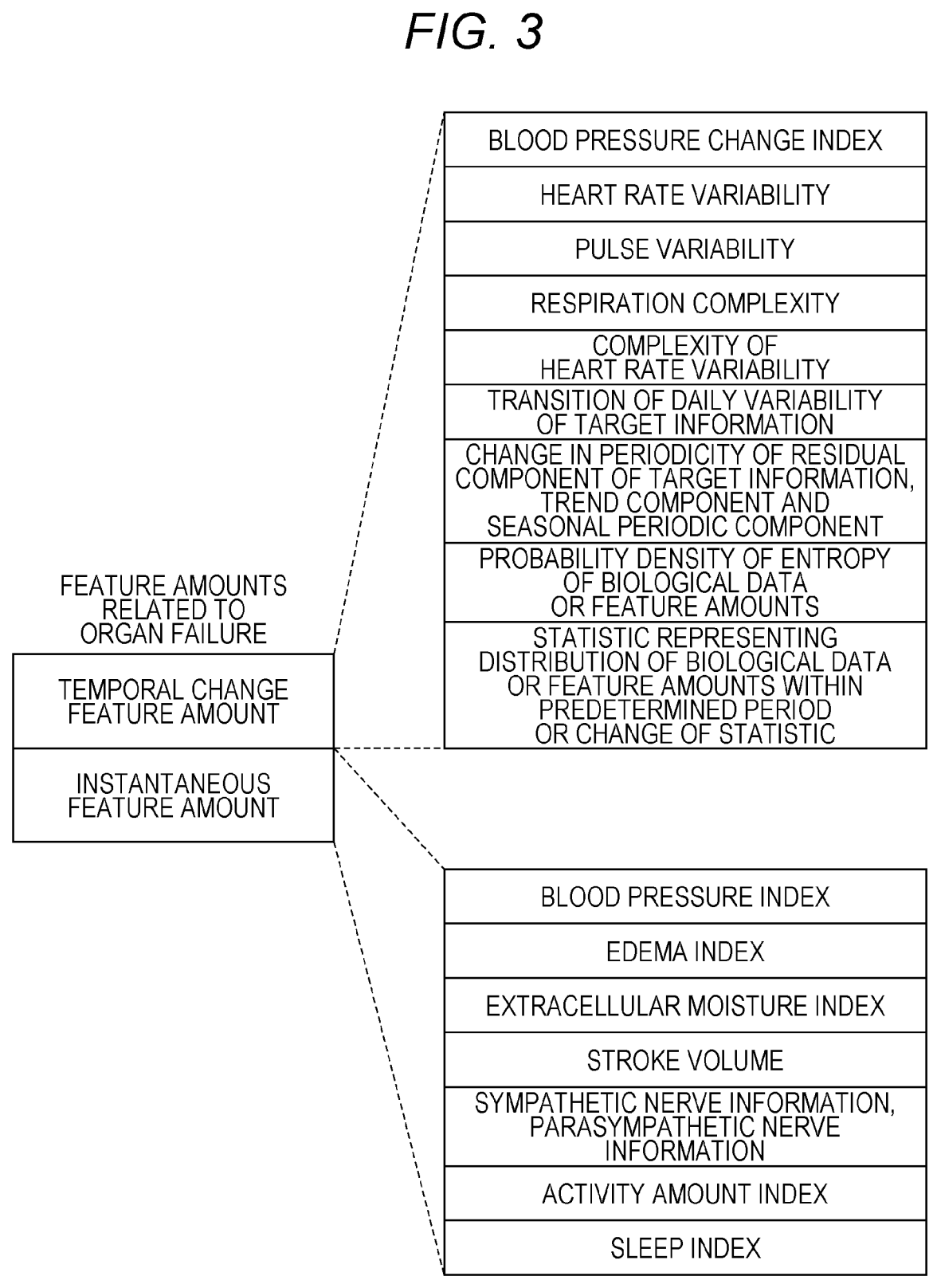

FIG. 3 is a view illustrating an example of feature amounts related to organ failure. The feature amounts related to the organ failure can be divided into, for example, a temporal change feature amount that is a feature amount capturing a temporal change and an instantaneous feature amount that is a feature amount of a value at the moment.

The temporal change feature amount can include a blood pressure change index, heart rate variability, pulse variability, a respiration complexity, a complexity of the heart rate variability, transition of daily variability of target information (tendency target information), change in periodicity of a residual component of the target information (tendency target information), a trend component and a seasonal periodic component, probability density of entropy of biological data or feature amounts, a statistic representing distribution of the biological data or the feature amounts within a predetermined period and a change of the statistic, and the like.

In other words, the feature amounts include a temporal change feature amount that captures a temporal change in a state of the target patient based on time-series data obtained within a predetermined period of the biological data.

The temporal change feature amount may include at least one of a blood pressure change index, heart rate variability, pulse variability, a respiration complexity, and a complexity of the heart rate variability.

The temporal change feature amount may include at least one of a residual component and a trend component separated from tendency target information including at least one of biological data or feature amounts obtained by processing the biological data, or a change in periodicity of a seasonal periodic component separated from the tendency target information.

In addition, the temporal change feature amount may include the biological data and the probability density of at least one entropy of the feature amounts obtained by processing the biological data.

The entropy can be calculated using a method such as permutation entropy, for example, in order to analyze time-series data that changes with complexity. As a result, a statistical complexity of the time-series data can be obtained, and a periodic signal, a chaotic signal, or the like, can be determined. Note that calculation of entropy is not limited to permutation entropy.

The instantaneous feature amount can include a blood pressure index, an edema index, an extracellular water index, a stroke volume, sympathetic nerve information, parasympathetic nerve information, an activity amount index, a sleep index, and the like.

The blood pressure index is a feature amount correlated with a blood pressure and can include, for example, an arterial pressure (ABP), a pulse transit time (PTT), and the like, which can be estimated on the basis of a pulse waveform of the photoelectric plethysmography function 203.

The edema index can be calculated as a ratio of an extracellular water to a total body water, both of which are measured by the impedance measurement function 201. The edema index also can be calculated as a ratio of an extracellular water resistance to an intracellular water resistance value, both of which are also measured by the impedance measurement function 201.

The extracellular water index can be calculated on the basis of the extracellular water resistance value, which is measured by the impedance measurement function 201. For example, a value obtained by multiplying the extracellular water resistance value by a minus can be used as the extracellular water index because the extracellular water resistance value is inversely proportional to the extracellular water.

The stroke volume is a blood volume sent from the heart per heartbeat and can be estimated on the basis of the pulse waveform of the photoelectric plethysmography function 203.

The sympathetic nerve information and the parasympathetic nerve information can be estimated from pulse wave data, heart rate data, and the extracellular water resistance value. As the sympathetic nerve information, a blood vessel hardening state index can be calculated from a change in trend of the extracellular water resistance value, and the calculated hardening state index can be used as the sympathetic nerve information. In the parasympathetic nerve information, the pulse variability can be calculated from the pulse wave or the heart rate, and (low-frequency component/high-frequency component) can be calculated as the parasympathetic nerve information on the basis of a power spectrum of the pulse variability. In a case where a value of (low frequency component/high frequency component) is large, the sympathetic nerve is dominant, and in a case where the value is small, the parasympathetic nerve is dominant.

The activity amount index includes a value counted each time a value of the acceleration sensor becomes greater than or equal to a predetermined value, the number of steps of a target patient, and the like.

The sleep index can be, for example, sleeping hours of the target patient and can be estimated from acceleration data, pulse data, heart rate data, and the like.

Note that the biological data or the feature amounts obtained by processing the biological data may be divided into during sleep and during non-sleep using the estimated sleeping hours. Variability during the night contributes to evaluation of exacerbation of heart failure. For example, if exacerbation occurs, it becomes difficult to breathe due to pulmonary congestion, and a statistic of the respiratory rate during sleep fluctuates. In addition, if exacerbation occurs, the heart function decreases, and thus, movement becomes difficult, and a statistic of the activity amount during non-sleep fluctuates. In addition, if exacerbation occurs, the number of times of turning over increases due to urination or deterioration of the cardiac function, or the number of times of toilet decreases, so that the statistic of the activity amount during sleep fluctuates.

The blood pressure change index only requires to be an index representing a change in the blood pressure index.

The heart rate variability is a feature amount representing a change in a time interval between heartbeats.

The pulse variability is a feature amount representing a change in a time interval between pulses.

The respiration complexity is a feature amount representing irregularity of respiration calculated using entropy, or the like, from a time series of a respiratory rate which is a respiratory rate per minute. Entropy fluctuates in a case where regularity of the change in the respiratory rate increases or decreases from normal times.

The complexity of the heart rate variability is a feature amount representing irregularity of the heart rate variability calculated from a time series of the heart rate variability using entropy, or the like. For example, if exacerbation occurs, the cardiac function deteriorates, and the value of the heart rate variability is more likely to decrease, so that entropy increases.

The transition of the daily variability of the target information (tendency target information) can be, for example, a feature amount representing the transition of the variability of the water content in one day. The variability of the water content can be estimated from, for example, the extracellular water resistance value.

The feature amount related to the target information (tendency target information) includes a change in periodicity of the residual component, the trend component, and the seasonal periodic component. The residual component, the trend component, and the seasonal periodic component can be separated by, for example, a seasonal autoregressive integrated moving average (SARIMA) model which is an analysis method of time-series data.

Figure 4:
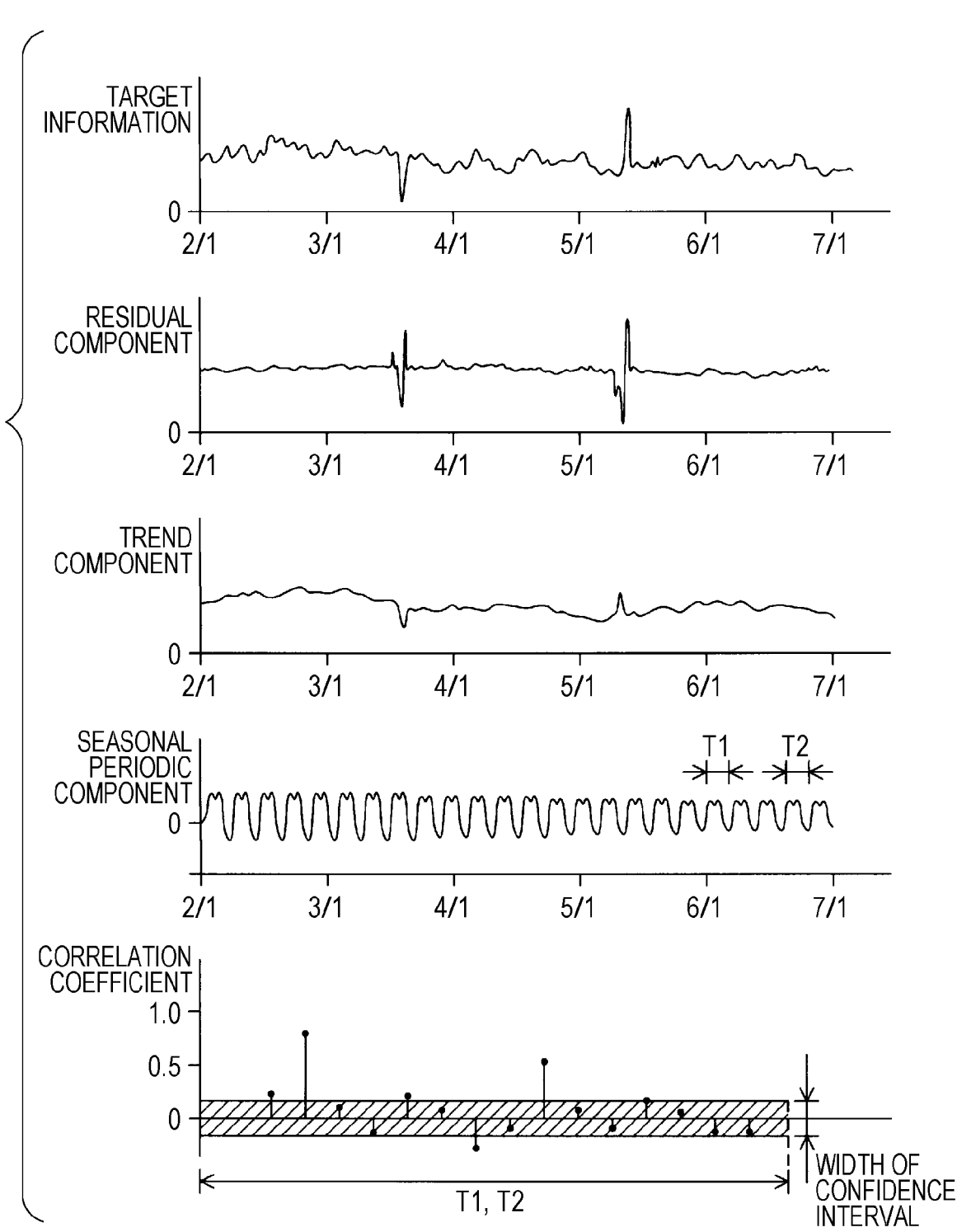
FIG. 4 is a view illustrating an example of feature amounts related to target information (tendency target information).

FIG. 4 is a view illustrating an example of feature amounts related to the target information (tendency target information). FIG. 4 schematically illustrates the target information, the residual component, the trend component, the seasonal periodic component, and a correlation coefficient. The target information (tendency target information) is time-series data to be analyzed and can include, for example, the biological data illustrated in FIG. 2 and the feature amounts (where the feature amount related to the target information (tendency target information) is excluded) illustrated in FIG. 3.

The residual component is a component indicating irregular and short-term fluctuation, the trend component is a component indicating monotonous fluctuation, and the seasonal periodic component is a component indicating regularly repeated fluctuation. The change in periodicity of the seasonal periodic component can be calculated, for example, as follows: the seasonal periodic component is separated for each of a comparison target section (a period T2 in the example of FIG. 4) and a section including the present time (a period T1 in the example of FIG. 4), and autocorrelation or biased autocorrelation is calculated for each periodic component. For the comparison target section and the section including the present time, a difference in a width of a confidence interval of the correlation coefficient of autocorrelation or biased autocorrelation is calculated as the change in periodicity. In FIG. 4, the correlation coefficient is calculated for each of the periods T1 and T2, and the width of the confidence interval (in FIG. 4, the width of a hatched region) is calculated. The width of the seasonal periodic component can also be used as the feature amount.

The probability density of the entropy of the biological data or the feature amounts can capture a change in irregularity of the biological data or the feature amounts.

FIGS. 5A and 5B are views illustrating an example of the probability density of the biological data and the feature amounts and the probability density of the entropy of the biological data and the feature amounts. In the example of FIGS. 5A and 5B, the respiratory rate is cited as an example of the biological data, and the pulse variability is cited as an example of the feature amount. As illustrated in FIG. 5A, it can be difficult to grasp a change in the probability density of the pulse variability between a steady state (graph indicated by a broken line) and the time immediately before exacerbation (graph indicated by a solid line). On the other hand, it can be seen that the probability density of the entropy of the pulse variability easily changes between the steady state (graph indicated by the broken line) and the time immediately before exacerbation (graph indicated by the solid line). In addition, as illustrated in FIG. 5B, it can be difficult to grasp a change in probability density of the respiratory rate between the steady state (graph indicated by the broken line) and the time immediately before the exacerbation (graph indicated by the solid line). On the other hand, it can be seen that the probability density of entropy of the respiratory rate easily changes between the steady state (graph indicated by the broken line) and the time immediately before the exacerbation (graph indicated by the solid line). Note that the probability density of the biological data and the feature amount can also be used as the feature amount.

Although the probability density of the entropy of the biological data or the feature amount can be used as the feature amount, the feature amount is not limited to the probability density of the entropy of the biological data or the feature amount, and a change (degree of change) in the probability density of the entropy, for example, may be used as the feature amount. The change (degree of change) in the probability density of entropy can be calculated, for example, as follows: the entropy is calculated using sample entropy, or the like, on the basis of time series data of the biological data or the feature amount. The time-series data of the biological data or the feature amount can be, for example, a time-series analyzed by SARIMA, a residual component from which the seasonal periodic component and the trend component are removed is extracted, and entropy of the extracted residual component is calculated. For each entropy described above, the time series is divided into the past and the latest in a certain time window to generate two groups. The probability density is estimated for the generated two groups, and two probability density ratios are calculated by Kullback-Leibler (KL) divergence, or the like, to obtain a feature amount as a change amount of irregularity. The time series of the feature amount (degree of change in the probability density) is calculated by sliding the above processing in a time axis direction and performing calculations at regular intervals.

A statistic representing the distribution of the biological data or the feature amount within the predetermined period or a change in the statistic can be used as a new feature amount. The statistic can be, for example, a median, a mode, a standard deviation, a second quartile, a third quartile or the like, regarding the distribution. A temporal change can be captured by setting a difference between the statistic of the distribution in the past period and the statistic of the distribution in the latest period as a difference in the statistic.

The control unit 60 has a function as a patient data acquisition unit and acquires medical information of the target patient to be evaluated for exacerbation from the data accumulation unit 20. In addition, the control unit 60 can acquire medical information of all organ failure patients not limited to the target patient from the data accumulation unit 20.

FIG. 6 is a view illustrating an example of the medical information. The medical information includes patient attribute information, disease information, diagnosis information, treatment information, medication information, and the like. Note that the medical information may be only part of these (for example, patient attribute information, disease information, and the like).

The patient attribute information can include an identifier (ID), name, gender, age, an address, a family structure, an occupation, a height, a weight, and the like, of the patient.

The disease information can mainly include a disease history of the patient and includes, for example, information such as at which timing or in which period the patient has been treated or admitted to the hospital for what disease.

The diagnosis information can include a diagnosis result of a doctor for the patient or history information of the diagnosis result.

The treatment information can mainly include a treatment history of the patient and can include, for example, information such as what treatment was performed at which timing or during which period.

The medication information can mainly include a medication history of the patient and includes, for example, information such as what drug was administered at which timing or during which period.

The medical information may also include medical knowledge possessed by a doctor or a specialized doctor skilled in organ failure, medical knowledge described in papers and specialized journals regarding organ failure, and domain knowledge such as medical experience of the specialized doctor.

In the present specification, the biological data, the feature amounts, and the medical information of the patient (including the target patient) are also collectively referred to as patient data. Note that the patient data may include season information depending on the month and day (date on the calendar) based on a time stamp recorded in the biological data. The body component, the blood pressure, the heart rate, and the like, have seasonal variability, and in order to consider the seasonal variability, the date at which the biological data is acquired is essential. It is therefore possible to improve prediction accuracy of exacerbation by predicting exacerbation using the patient background group or generating the prediction model in consideration of the season information on the basis of the date (date on the calendar) based on the timestamp recorded in the biological data. Note that the main factors of the seasonal variability are a temperature and humidity, and thus, the season information can be made more accurate and divided finely by specifying a region on the basis of the address of the patient and position information obtained by, for example, the GPS (global positioning satellite) built in the wearable device 200, using a monthly average temperature of the specified region, and further using a temperature and humidity of the day from the Meteorological Agency data, or the like. Next, the background of the patient will be described.

In a case where patients with organ failure (for example, heart failure, or the like) are gathered as organ failure patients in one group, and exacerbation is predicted, there is a case where sufficient prediction accuracy cannot be obtained. In other words, if the background (patient background) of each patient with organ failure is different, the influence of the patient background on a factor of the organ failure may also change, and thus it can be difficult to improve the accuracy if exacerbation is predicted without determining the patient background. The patient background can include, for example, information such as patient attributes (for example, gender, age, a height, a weight, and the like), patient biological data, various feature amounts obtained by processing the biological data, patient disease information, diagnosis information, treatment information, and medication information.

In order to construct a patient background group, it can be necessary to collect a large number of past patient data. The patient data can be collected by the data collection device 300, but may be collected by the exacerbation prediction device 100. In the following description, it is assumed that the control unit 60 collects the patient data.

Figure 7:
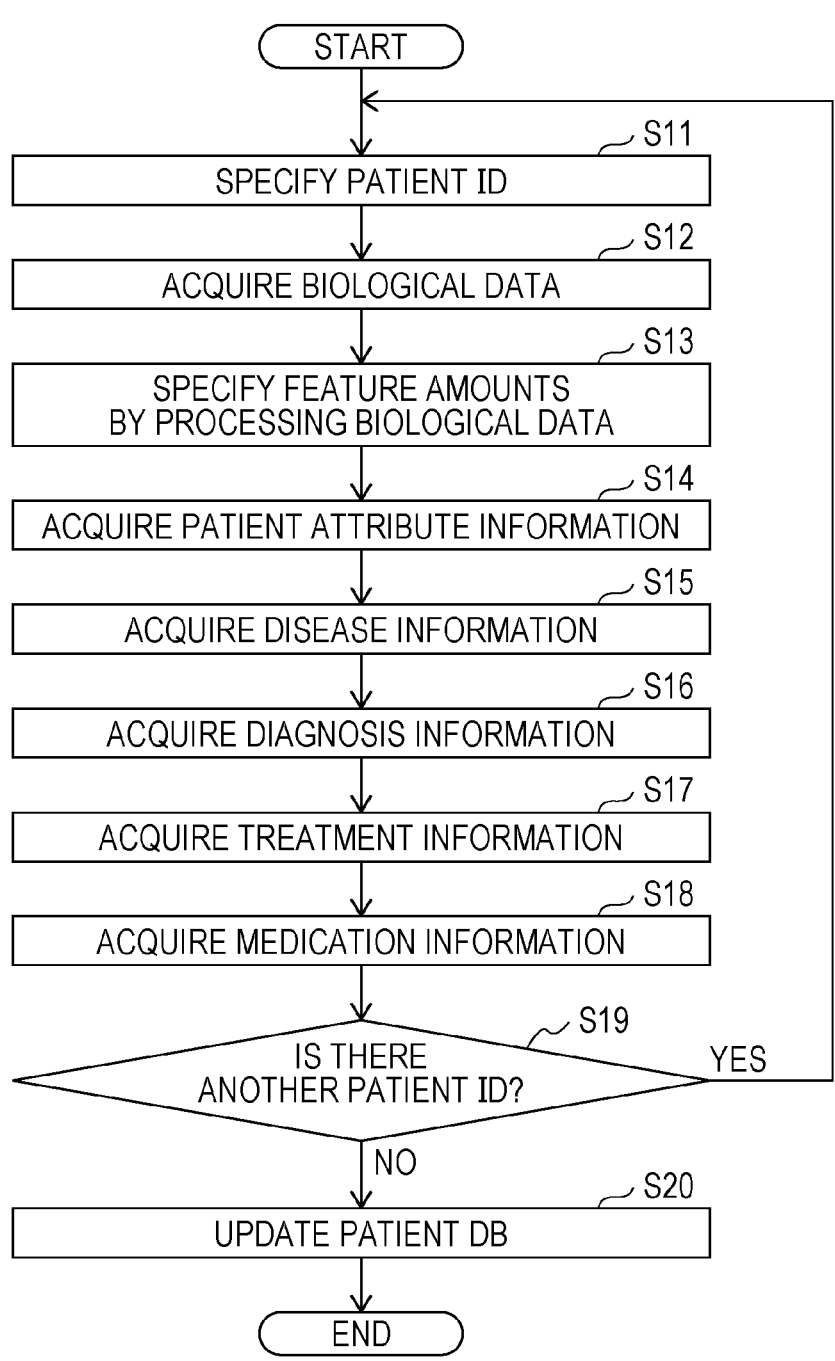
FIG. 7 is a view illustrating an example of patient data collection processing.

FIG. 7 is a view illustrating an example of patient data collection processing. The control unit 60 specifies a patient ID (S11) and acquires biological data of the specified patient ID (S12). The biological data includes not only data at a certain time point or time series data of a certain period but also history data of a past time point or period. The biological data is exemplified in FIG. 2, for example. The control unit 60 processes the biological data to specify the feature amounts using the feature amount specification function 61 (S13). The feature amounts are exemplified in FIG. 3, for example.

The control unit 60 acquires patient attribute information (S14), disease information (S15), diagnosis information (S16), treatment information (S17), and medication information (S18). Note that, depending on the patient, all of the diagnosis information, the treatment information, and the medication information may not be acquirable. In this case, it is only necessary to acquire only the acquirable medical information. The control unit 60 may acquire domain knowledge.

The control unit 60 determines whether or not there is another patient ID (S19), and if there is another patient ID (S19: Yes), continues the processing from step S11. In a case where there is no other patient ID (S19: No), the control unit 60 updates the patient DB (S20) and ends the processing.

FIG. 8 is a view illustrating an example of a configuration of the patient DB. As illustrated in FIG. 8, in the patient database (DB), patient attribute information, a biological data history, a feature amount history, a disease history, a diagnosis history, a treatment history, and a medication history are recorded in association with each other for each patient ID. The patient DB is stored in the data accumulation unit 20 of the exacerbation prediction device 100, but is not limited to the patient DB stored in the data accumulation unit 20 of the exacerbation prediction device 100, and the patient DB may be stored in the data accumulation unit 302 of the data collection device 300.

The patient background group construction function 62 pre-constructs a patient background group of organ failure (for example, heart failure, or the like) on the basis of the patient data recorded in the patient DB.

Figure 9:
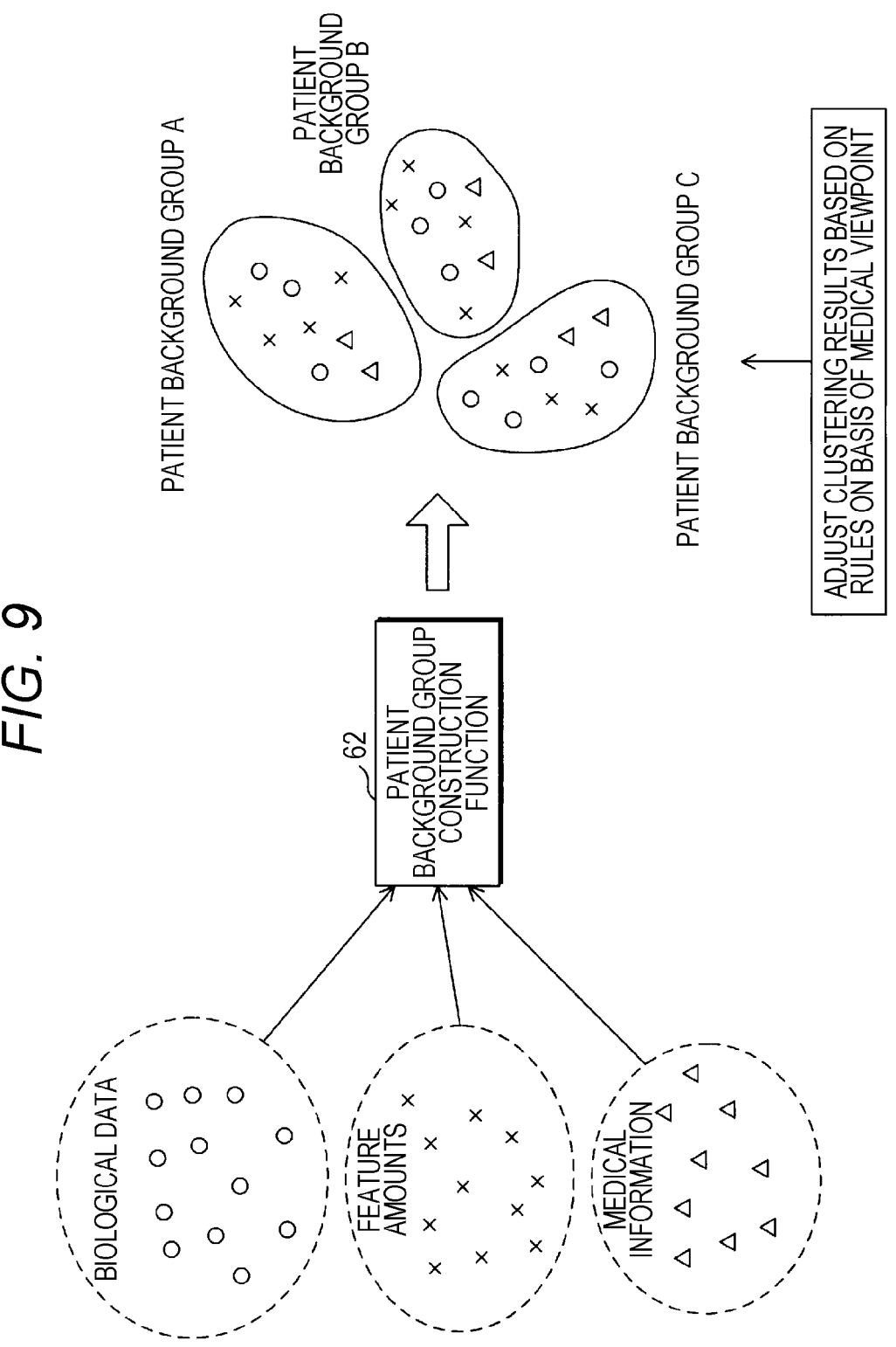
FIG. 9 is a view illustrating an example of construction of a patient background group.

FIG. 9 is a view illustrating an example of construction of the patient background group. The patient background group construction function 62 performs clustering on the basis of the patient data (including biological data, the feature amount and the medical information) of a large number of past patients, for example, using a k-means method and classifies the patient data into a predetermined number of clusters. Note that the clustering method is not limited to the k-means method. In the example of FIG. 9, the number of clusters is three, and the patient data is classified into three groups such as patient background groups A, B, and C. The number of clusters is not limited to three. For example, the patient data may be classified into patient background groups A, B, C, D, . . . . In this manner, a large number of past patient data can be classified into patient background groups by a required clustering algorithm.

Next, with respect to the patient background groups A, B, and C mechanically classified by the clustering algorithm, the clustered results may be adjusted on the basis of a medical viewpoint or domain knowledge possessed by a specialized doctor or a skilled doctor of organ failure. In addition, a specialized doctor, or the like, may check and adjust the clustered results, which results in making it possible to construct patient background groups in which the medical viewpoint and the domain knowledge are considered.

As the patient data (time-series data) to be input to the patient background group construction function 62, feature information extracted by pre-learning by an auto encoder, or data reduced in dimension (for example, three dimensions, and the like) by time delay embedding, or the like, may be used. In heart failure, if the primary diseases such as myocardial infarction, arrhythmia, and respiratory failure, which cause heart failure are different, the biological data that changes at the time of exacerbation and various feature amounts obtained by processing the biological data are also greatly different. Thus, to predict exacerbation of heart failure, it is preferable that the control unit 60 acquire disease information including primary disease information of heart failure and then construct patient background groups in advance on the basis of patient data including the primary disease information of heart failure. Note that the patient background groups thus constructed can be, for example, groups for each of the primary diseases of heart failure including at least myocardial infarction, arrhythmia, and respiratory failure.

Next, a prediction model for predicting exacerbation will be described.

First, a method of constructing a prediction model for each patient background group will be described.

The prediction model learning function 64 (control unit 60) acquires training data including patient data of a plurality of patients, classifies the acquired training data into training data for each of a plurality of patient background groups, and generates one or more prediction models for predicting exacerbation for each of the patient background groups using the classified training data.

Figure 10:
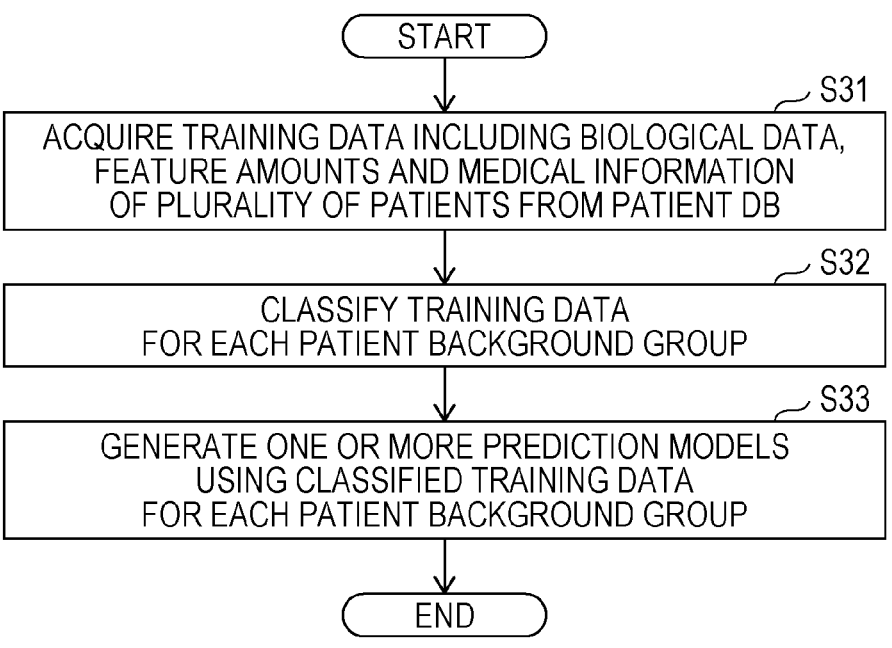
FIG. 10 is a view illustrating an example of prediction model generation processing.

FIG. 10 is a view illustrating an example of prediction model generation processing. The control unit 60 acquires training data including patient data (the biological data, the feature amounts, the medical information, and the like) of a plurality of patients from the patient DB (see FIG. 8) (S31). The control unit 60 classifies the training data into patient background groups (S32). The patient background groups can be classified into patient background groups A, B, and C, for example, using the method illustrated in FIG. 9.

The control unit 60 generates one or more prediction models using the classified training data for each of the patient background groups (S33) and ends the processing. Details of generation of the prediction model will be described later.

Figure 11:
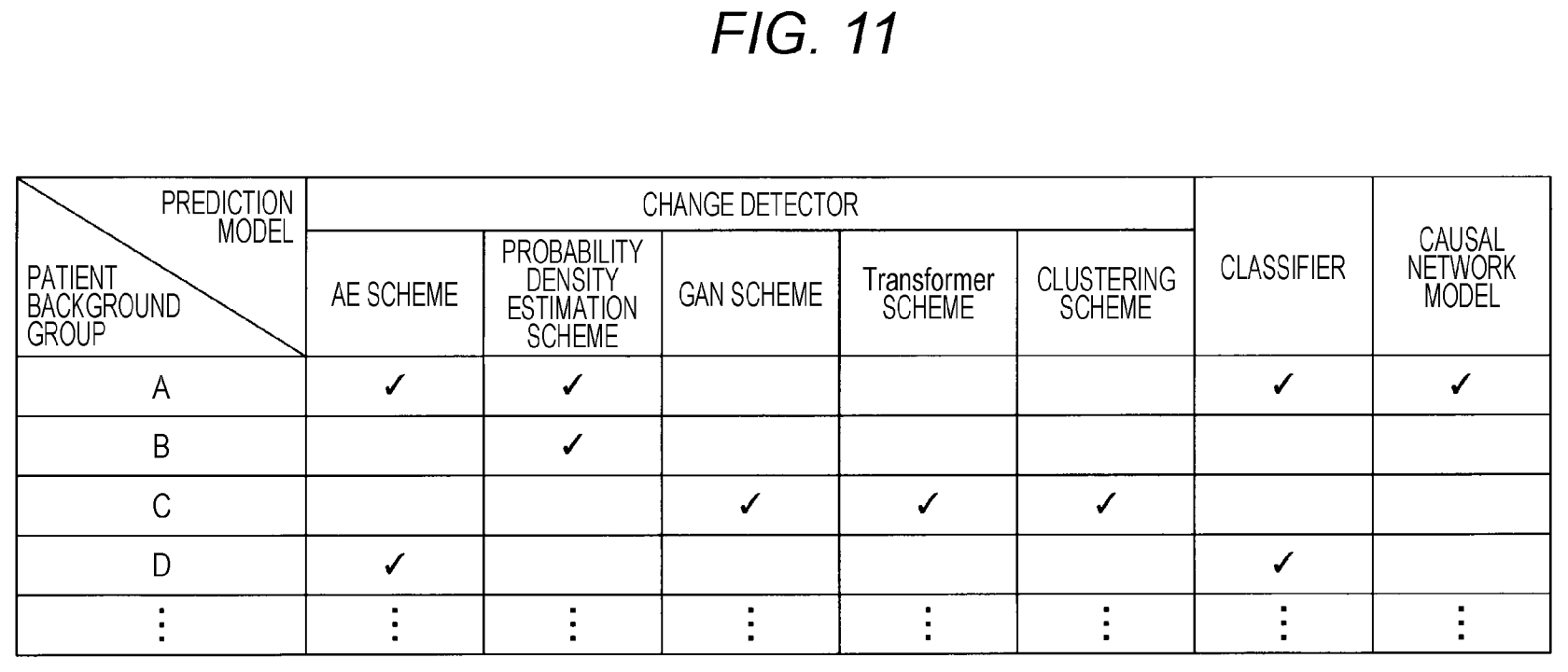

FIG. 11 is a view illustrating an example of a patient background group/prediction model table. The patient background group/prediction model table is a table in which a prediction model is associated with each of a plurality of patient background groups. As illustrated in FIG. 11, types of the prediction model can include a change detector, a classifier, and a causal network model, and types of the change detector can include an auto encoder (AE) scheme, a probability density estimation scheme, a generative adversarial network (GAN) scheme, a Transformer scheme, and a clustering scheme. Note that the types of the prediction model are not limited to the example of FIG. 11.

It is assumed that there are patient background groups A, B, C, D, . . . . In the patient background group A, a change detector, a classifier, and a causal network model are constructed, and further, the change detector includes an AE scheme and a probability density estimation scheme. In the patient background group B, a change detector is constructed, and further, the change detector includes a probability density estimation scheme. In the patient background group C, a change detector is constructed, and further, the change detector can include a GAN scheme, a Transformer scheme, and a clustering scheme. In the patient background group D, a change detector and a classifier are constructed, and further, the change detector includes an AE scheme. As described above, the number of prediction models to be constructed (generated) for each patient background group may be one or more. The patient background group/prediction model table illustrated in FIG. 11 can be stored in the storage unit 70.

In FIG. 11, the AE scheme is prepared for the patient background groups A and D, but the AE scheme of each of the patient background group A and the patient background group D is not the same, and parameters of the prediction model are adjusted in an optimum form for each patient background group. The same applies to the probability density estimation scheme prepared for the patient background groups A and B and the classifier prepared for patient background groups A and D.

In addition, the control unit 60 acquires past biological data of a large number of patients and specifies feature amounts related to organ failure obtained by processing the acquired biological data. The control unit 60 can generate a prediction model so as to predict exacerbation of the patient on the basis of training data including the acquired biological data and the specified feature amounts in a case where the biological data and the feature amounts are input.

With the above-described configuration, as compared with a case where a prediction model is generated using only biological data of a large number of patients as training data, it is possible to construct a prediction model in consideration of characteristics for each case by generating a prediction model including feature amounts obtained by processing the biological data in the training data.

Next, selection of a prediction model suitable for the patient background group and prediction of exacerbation by the selected prediction model will be described.

The control unit 60 acquires patient data of the target patient to be evaluated for exacerbation. The patient background group selection function 63 (patient background group selection unit) selects a patient background group to which the target patient belongs from a plurality of patient background groups classified by patient data of a plurality of patients collected in advance. As a method of selecting a patient background group, there is a method of selecting a patient background group to which the target patient belongs on the basis of at least part of the acquired patient data of the target patient. Specifically, there are methods in which (1) the patient background group is selected using the patient data of the target patient including initial biological data measured by a device such as the wearable device 200 and is not changed thereafter, (2) the patient background group is re-selected using the patient data of the target patient including the biological data of a predetermined period measured by the device at predetermined intervals (for example, for each season, etc.), (3) the patient background group is re-selected using the patient data of the target patient including the biological data measured by the device and to be input to the prediction model each time the prediction is performed, (4) the patient background group is selected using initial medical information among the acquired patient data of the target patient and is not changed thereafter, and (5) the patient background group is re-selected using the latest medical information among the acquired patient data at predetermined intervals (for example, for each season, etc.), and (6) the patient background group is re-selected using the latest medical information among the acquired patient data of the target patient each time prediction is performed. The prediction model selection function 65 (the prediction model selection unit, the prediction model calling unit) selects or calls one or more prediction models corresponding to the patient background group to which the target patient belongs from one or more prediction models prepared in advance for each of the plurality of classified patient background groups. The prediction model execution function 66 (control unit 60) inputs the acquired patient data to the selected or called prediction model to predict exacerbation of the target patient.

FIG. 12 is a view illustrating a first example of prediction model execution processing. The processing illustrated in FIG. 12 indicates the selection method (3) described above. The control unit 60 acquires the biological data of the target patient to be evaluated for exacerbation (S41). The biological data is illustrated in FIG. 2. The control unit 60 processes the acquired biological data and specifies feature amounts (S42). The feature amounts are illustrated in FIG. 3.

The control unit 60 acquires medical information including patient attribute information, disease information, diagnosis information, treatment information, and medication information of the target patient (S43). The medical information may include domain knowledge. The control unit 60 selects a patient background group to which the target patient belongs from a plurality of patient background groups classified in advance (S44). Furthermore, the control unit 60 may receive, from a doctor, or the like, operation of selecting a patient background group to which the target patient belongs from a plurality of patient background groups classified by patient data of a plurality of patients collected in advance and select the patient background group to which the target patient belongs according to the received operation.

The control unit 60 selects one or more prediction models corresponding to the patient background group to which the target patient belongs from one or more prediction models prepared in advance for each of a plurality of patient background groups (S45), inputs the biological data, the feature amounts and the medical information of the target patient to the selected prediction model to predict exacerbation of the target patient (S46) and ends the processing.

By using the patient background group/prediction model table stored in the storage unit 70, the control unit 60 (the prediction model selection function 65, the prediction model selection unit) may execute the processing from S44 (patient background group selection processing) to S45 (prediction model selection processing) described above. In other words, the prediction model selection function 65 may include the patient background group selection function 63. As a result, the prediction model selection function 65 functions to select the patient background group to which the target patient to be evaluated for exacerbation belongs from the plurality of patient background groups stored in the storage unit 70, thereby selecting one or more prediction models corresponding to the patient background group to which the target patient belongs from the one or more prediction models stored in the storage unit 70.

In a case of the selection method (1) or (4) among the above-described methods of selecting a patient background group, the processing of S44 is skipped after the group is selected first. Furthermore, in a case of the selection method (2) among the above-described methods of selecting a patient background group, in a case where the interval is not a predetermined interval, S44 is skipped.

With the above-described configuration, the patient background group to which the target patient belongs is selected from a plurality of patient background groups according to the patient background, and thus, it is possible to predict exacerbation more depending on the patient background than a case where exacerbation is determined for one group of organ failure patients, so that it is possible to improve accuracy of prediction of exacerbation of patients with organ failure. In particular, in prediction of exacerbation of heart failure, it is preferable that the patient background group is constructed on the basis of patient data including primary disease information of heart failure, and the primary disease information of heart failure is included as the disease information in the patient data of the target patient acquired by the control unit 60. As a result, the patient background group to which the target patient belongs is selected in consideration of the primary disease of heart failure, so that it is possible to predict exacerbation of heart failure more depending on the patient background and to further improve accuracy of prediction of exacerbation of heart failure patients. Specifically, for example, a patient background group that matches the primary disease of heart failure of the target patient is selected from patient background groups that are groups for each of the primary diseases of heart failure including at least myocardial infarction, arrhythmia, and respiratory failure, and a prediction model constructed from a large number of pieces of past patient data including the same primary disease information is selected. It is therefore possible to more accurately predict exacerbation of the heart failure patient.

In addition, exacerbation of the target patient can be predicted only by inputting the patient data to the prediction model corresponding to the patient background group of the target patient, which helps enable even a doctor who is not a skilled doctor or a specialized doctor to easily determine exacerbation of the target patient.

The control unit 60 has a function as a prediction unit, acquires biological data of the target patient to be evaluated for exacerbation, specifies feature amounts related to organ failure obtained by processing the acquired biological data, and inputs at least part of patient data including the acquired biological data and the specified feature amounts to a prediction model for predicting exacerbation of the patient to predict exacerbation of the target patient. Note that, as described above, the prediction unit includes functions of both the prediction model execution function 66 and the exacerbation score calculation function 67.

The feature amounts include those illustrated in FIG. 3. The control unit 60 may select the feature amounts to be used for the target patient on the basis of a medical viewpoint regarding a physical mechanism for each case (arrhythmia, cardiomyopathy, etc.) of the target patient. In addition, the doctor may select the feature amounts to be used for each target patient using domain knowledge of a specialized doctor, or the like.

With the above-described configuration, not only the biological data of the target patient but also the feature amounts specified from the biological data is input to the prediction model, whereby exacerbation can be predicted for patients of various backgrounds in consideration of characteristics for each case.

The control unit 60 may acquire medical information based on at least one of patient attribute information, disease information, diagnosis information, treatment information, or medication information of the target patient and input at least part of the acquired medical information to the prediction model to predict exacerbation of the target patient. This results in making it possible to consider different medical information for each patient such as a patient attribute, a disease history, a diagnosis history, a treatment history, a medication history, and the like, so that it is possible to flexibly predict exacerbation according to the patient instead of uniformly predicting exacerbation.

The feature amounts to be used together with the biological data include a temporal change feature amount that captures a temporal change in a state of the target patient based on the time-series data obtained within a predetermined period of the biological data. The temporal change feature amount may include at least one of a blood pressure change index, heart rate variability, pulse variability, a respiration complexity, and a complexity of the heart rate variability. In addition, the temporal change feature amount may include at least one of a residual component and a trend component separated from tendency target information including at least one of biological data or feature amounts obtained by processing the biological data, or a change in periodicity of a seasonal periodic component separated from the tendency target information. In addition, the temporal change feature amount may include the biological data and the probability density of at least one entropy of the feature amounts obtained by processing the biological data. Which feature amounts are included may be determined on the basis of a medical viewpoint regarding the physical mechanism of the target patient for each case. In other words, the feature amounts may be determined from a medical viewpoint in addition to a method of mechanically selecting a feature amount having a large amount of information or feature amount having a high contribution to the prediction model.

Next, a learning method (generation method) and an exacerbation prediction method will be described for each scheme of the prediction model. First, creation of learning data (training data) will be described.

Figure 13:
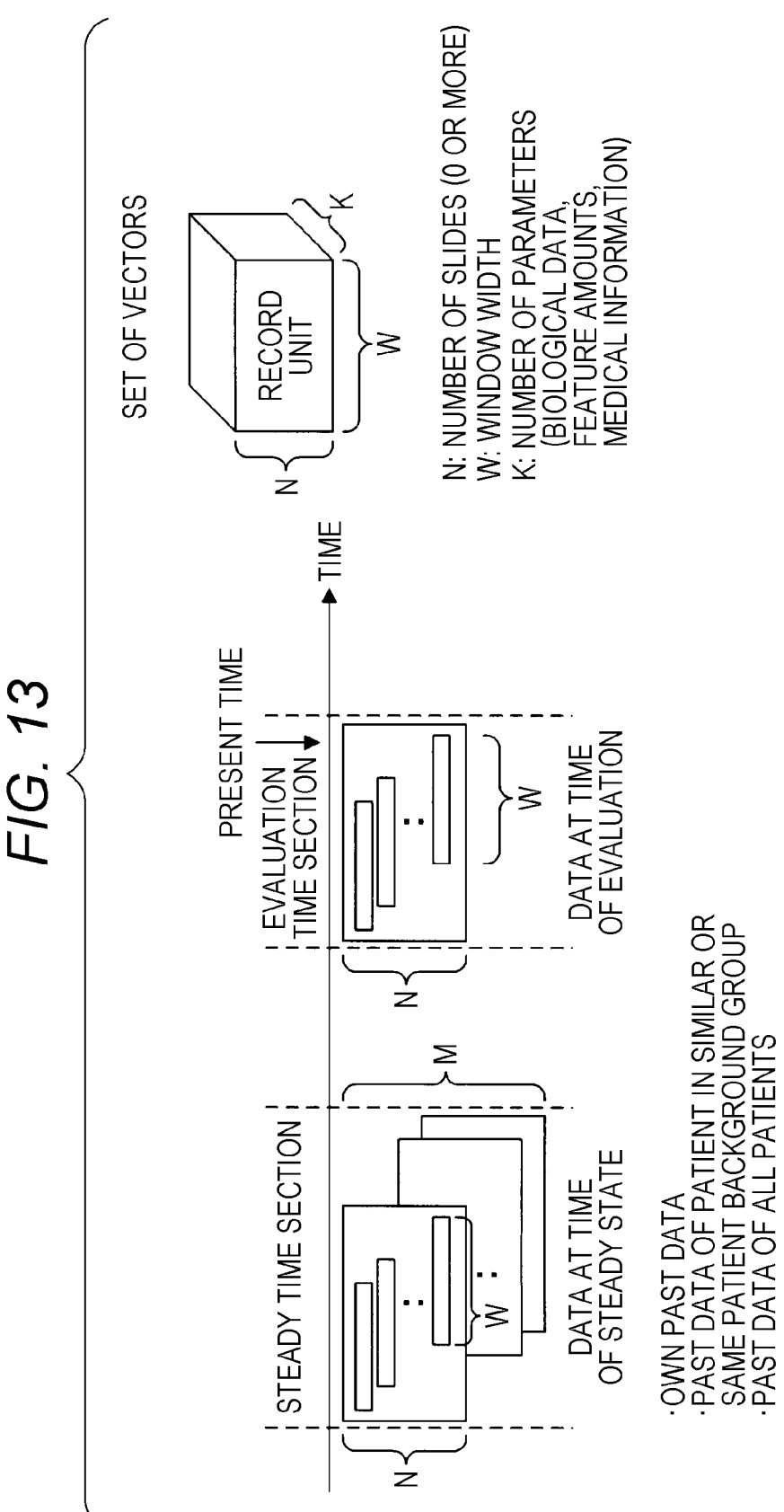
FIG. 13 is a view illustrating a first example of creation of learning data.

FIG. 13 is a view illustrating a first example of creation of learning data. The first example illustrates separation between data at the time of evaluation and data at the time of a steady state (i.e., condition of patient is not exacerbated). Data in the latest evaluation time section including present is set as the data at the time of evaluation, and data in the past steady time section is separated as the data at the time of the steady state. The data at the time of the steady state is data when the patient's condition is not exacerbated. The data at the time of the steady state may be, for example, one's own past data, patient data of a similar or the same patient background group, or past data of all patients.

A window width of the steady time section can be set as W. The window width W can be, for example, any of 6 hours, 12 hours, 24 hours, 2 to 7 days, or any of 2 to 4 weeks. Data in the window width can be slid by N (0 or more) to form a set of vectors. K is the number of types of patient data (the number of parameters). M is the number of pieces of the data at the time of the steady state in the steady time section. The data at the time of the steady state and the data at the time of evaluation are created for each patient background group.

FIG. 14 is a view illustrating a second example of creation of learning data. The second example illustrates separation of the data at the time of evaluation and data at the time of exacerbation. Data in the latest evaluation time section including present is used as the data at the time of evaluation, and data in the past exacerbation time section is separated as the data at the time of exacerbation. The data at the time of exacerbation is data when the patient's condition is exacerbated. The data at the time of exacerbation may be, for example, one's own past data, data of patients in a similar or the same patient background group, or past data of all patients. The window width W, the number of slides N, the number of parameters K, and the number of data M are the same as those in the first example (i.e., steady state). The data at the time of exacerbation and the data at the time of evaluation are created separately for each patient background group.

Next, each type of the prediction model will be described.

Figures 15A, 15B:
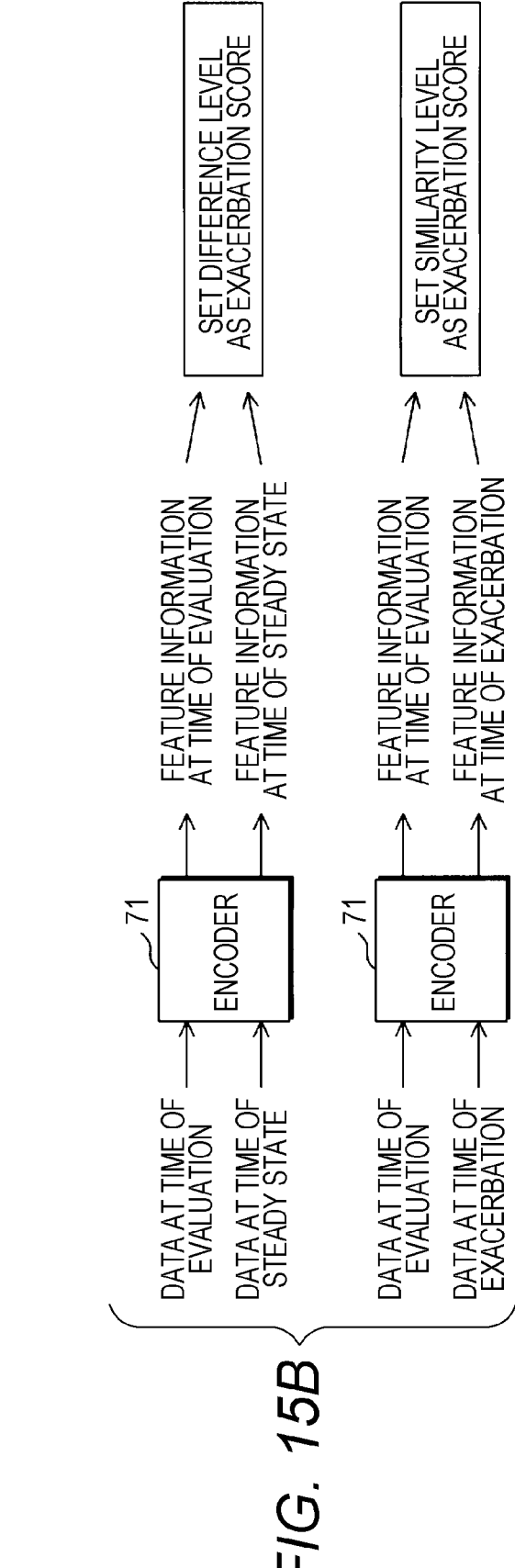
FIGS. 15A and 15B are views illustrating an example of an auto encoder scheme.

FIGS. 15A and 15B are views illustrating an example of an auto encoder scheme. The auto encoder (AE) 70 includes an encoder 71 and a decoder 72. FIG. 15A illustrates an example at the time of learning, and FIG. 15B illustrates an example at the time of prediction of exacerbation. As illustrated in FIG. 15A, in learning of the AE 70, parameters of the encoder 71 and the decoder 72 are adjusted such that training input data to be input to the AE 70 matches output data. The training input data includes the data at the time of the steady state and the data at the time of exacerbation described in FIGS. 13 and 14. The training input data is classified for each patient background group. In other words, learning (generation) of the AE 70 is performed for each patient background group. If the data at the time of the steady state is input to the encoder 71, the encoder 71 generates feature information (feature information at the time of the steady state) obtained by compressing the data at the time of the steady state. In addition, if the data at the time of exacerbation is input to the encoder 71, the encoder 71 generates feature information (feature information at the time of exacerbation) obtained by compressing the data at the time of exacerbation.

As described above, the training data classified for each patient background group includes patient data at the time of the steady state (data at the time of the steady state) of the patient, and the control unit 60 generates a feature output model (for example, an auto encoder) so as to output feature information at the time of the steady state (feature information at the time of the steady state) in a case where the patient data at the time of the steady state is input. Furthermore, the training data classified for each patient background group includes patient data at the time of exacerbation of the patient (data at the time of exacerbation), and the control unit 60 generates a feature output model (for example, an auto encoder) so as to output feature information at the time of exacerbation (feature information at the time of exacerbation) in a case where the patient data at the time of exacerbation is input.

As illustrated in FIG. 15B, at the time of prediction of exacerbation, exacerbation is predicted by comparing the feature information at the time of evaluation output by the encoder 71 in a case where the data at the time of evaluation of the target patient is input to the encoder 71 with the feature information at the time of the steady state output by the encoder 71 in a case where the data at the time of the steady state of the target patient is input to the encoder 71, and outputting a difference level between the two as an exacerbation score. The exacerbation score may be a continuous value (for example, 0 to 1) that represents a degree (level) of exacerbation or may be a binary value (0 and 1) that represents the presence or absence of exacerbation. Similarly, exacerbation is predicted by comparing the feature information at the time of evaluation output by the encoder 71 in a case where the data at the time of evaluation of the target patient is input to the encoder 71 with the feature information at the time of exacerbation output by the encoder 71 in a case where the data at the time of exacerbation of the target patient is input to the encoder 71, and outputting a similarity level between the two as the exacerbation score.

As described above, the prediction model includes a feature output model (for example, an auto encoder) that outputs feature information representing features of patient data in a case where the patient data of the target patient is input. The control unit 60 can predict exacerbation of the target patient on the basis of a change (different level) between the feature information (feature information at the time of the steady state) output by the feature output model in a case where patient data at the time of the steady state of the target patient is input to the feature output model and the feature information at the time of evaluation (feature information at the time of evaluation) output by the feature output model in a case where the patient data at the time of evaluation of the target patient is input to the feature output model.

Furthermore, the control unit 60 can predict exacerbation of the target patient on the basis of a change (similarity level) between the feature information at the time of exacerbation (feature information at the time of exacerbation) output by the feature output model in a case where patient data at the time of exacerbation of the target patient is input to the feature output model and the feature information at the time of evaluation (feature information at the time of evaluation) output by the feature output model in a case where patient data at the time of evaluation of the target patient is input to the feature output model.

In the example of FIG. 15, the auto encoder has been described as an example of the change detector (feature output model), but the change detector is not limited to the auto encoder. For example, instead of the auto encoder scheme, a GAN scheme or a Transformer scheme may be used.

In a case of the GAN scheme, a generator (generator) is caused to perform learning so as to output the feature information at the time of the steady state and the feature information at the time of exacerbation, and at the same time, a discriminator (discriminator) is caused to perform learning so as to be able to discriminate the steady state and exacerbation. At the time of prediction of exacerbation, exacerbation of the target patient can be predicted on the basis of the change in a result of the discrimination between the time of the steady state and exacerbation output by the discriminator with the feature information at the time of the steady state or the feature information at the time of exacerbation output by the generator to which the data at the time of evaluation has been input.

In the Transformer scheme, by using predicted next day data as a next decoder input, exacerbation for several days after the next day can be predicted one after another like a chain reaction. A statistic such as a median of predicted data for several days can be used as a predicted expected value, and a difference from the expected value for the past several days can be used as the exacerbation score.

Figure 16:
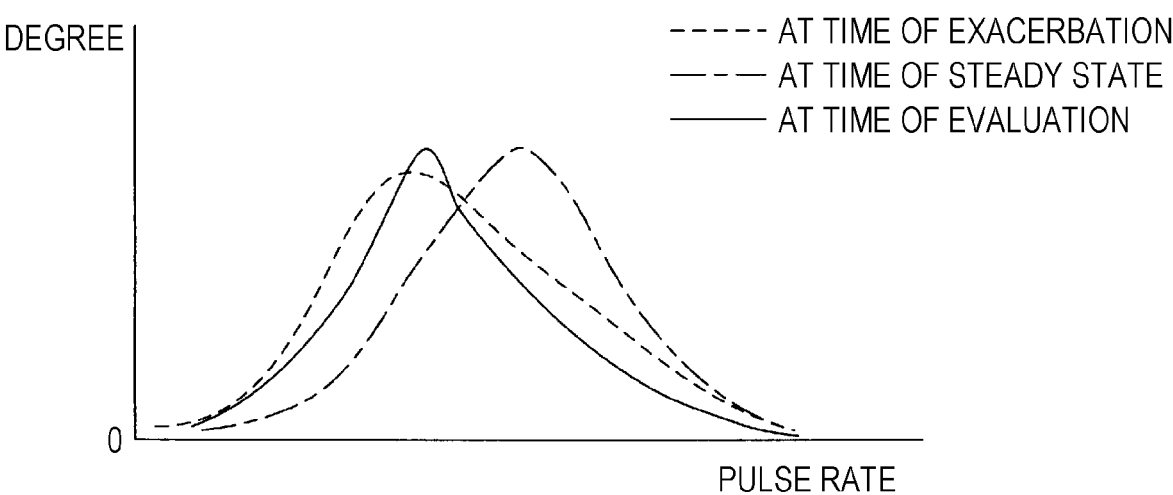
FIG. 16 is a view illustrating an example of a probability density estimation scheme.

FIG. 16 is a view illustrating an example of the probability density estimation scheme. In the probability density estimation scheme, the probability density at the time of the steady state, at the time of exacerbation, and at the time of evaluation of patient data such as biological data or feature amounts of the target patient is calculated, and the exacerbation score is calculated on the basis of an index representing a difference in the probability density. As the index, for example, Kullback-Leibler divergence (KLD: relative entropy), similarity, a density ratio, and the like, can be used. The probability density estimation scheme can be performed for each patient background group.

In the example of FIG. 16, the probability density of the pulse rate of a certain target patient is illustrated. The probability density at the time of evaluation is similar to the probability density at the time of exacerbation as compared to the probability density at the time of the steady state, and thus, the exacerbation score is a value close to the score at the time of exacerbation.

Figures 17A, 17B:
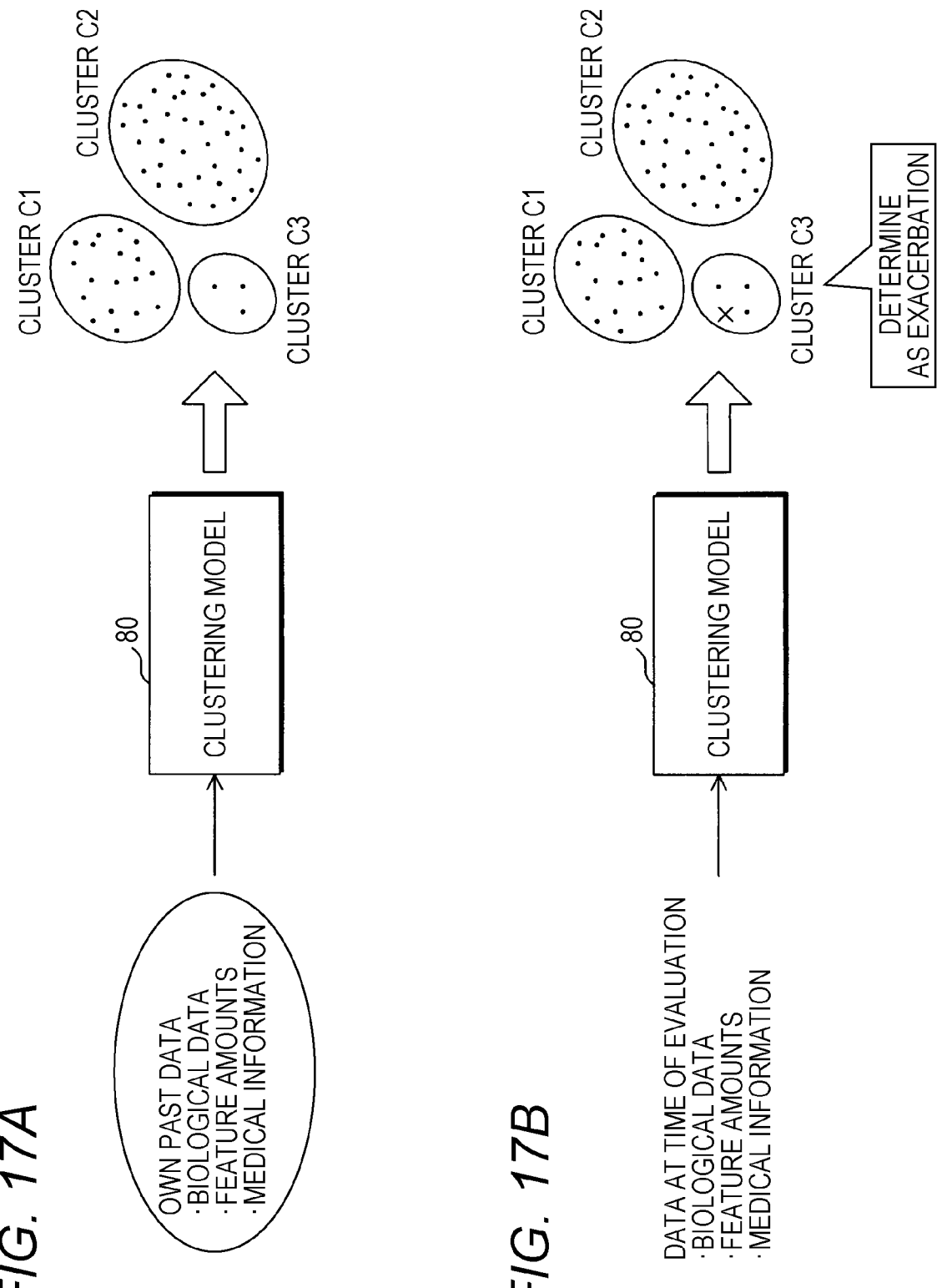
FIGS. 17A and 17B are views illustrating a first example of a clustering scheme.

FIGS. 17A and 17B are views illustrating a first example of the clustering scheme. FIG. 17A illustrates an example at the time of learning, and FIG. 17B illustrates an example at the time of prediction of exacerbation. As illustrated in FIGS. 17A, at the time of learning, past patient data (the biological data, the feature amounts, the medical information) of the target patient itself is input to the clustering model 80 to classify the patient into clusters. As a clustering method, k-means or deep clustering can be used, but the clustering method is not limited to k-means or deep clustering. In the example of FIG. 15A, it is assumed that the patient data is classified into clusters C1, C2, and C3. Here, the number of pieces of patient data included in the cluster C3 is smaller than the number of pieces of patient data included in the other clusters C1 and C2, and thus, the cluster C3 is set as an abnormal cluster.

As illustrated in FIG. 17B, at the time of prediction of exacerbation, patient data of the target patient is input to the clustering model 80, and exacerbation can be detected on the basis of whether or not a cluster (in the drawing, indicated with a reference numeral X) classified by the clustering model 80 is included in an abnormal cluster or whether a cluster most similar to the cluster is an abnormal cluster. In the example of FIG. 17B, the cluster classified by the clustering model 80 is included in the cluster C3 which is an abnormal cluster, and thus it can be determined as exacerbation. Learning and execution of the clustering scheme can be performed separately for each patient background group.

As described above, the prediction model includes a clustering model that classifies the patient data into clusters. The control unit 60 can predict exacerbation of the target patient on the basis of a plurality of clusters classified by inputting past patient data of the target patient to the clustering model and clusters classified by inputting patient data at the time of evaluation of the target patient to the clustering model.

FIG. 18 is a view illustrating a second example of the clustering scheme. As illustrated in FIG. 18, time-series data of patient data (the biological data, the feature amounts and the medical information) of the target patient for each predetermined period is input to the clustering model 80, and a clustering result for each predetermined period is generated. The predetermined period may be, for example, one day, any one of two days to six days, one week, two weeks, or the like. The clustering result is time-series data of cluster labels (in the example of FIGS. 18, C1, C2, and C3) for each predetermined period. It is assumed that the cluster label C3 represents an abnormal cluster with a small number of pieces of patient data included. In a case where the time series of the cluster labels are C1 and C2, it is determined as the steady state, but in a case where the cluster label C3 appears, it can be determined as exacerbation.

In addition, the time-series data of the cluster labels may be divided into constant window widths, and a change between data of the window width up to the previous day and data of the window width including today may be calculated as the exacerbation score. In this case, it is not necessary to specify an abnormal cluster in advance.

FIG. 19 are views illustrating an example of a classifier. FIGS. 19A and 19B illustrate an example at the time of learning, and FIG. 19C illustrates an example at the time of prediction of exacerbation. The classifier 90 can include, for example, a neural network such as a convolutional neural network (CNN), a recurrent neural network (RNN), or the like, but the classifier is not limited to CNN and RNN, and support vector machine (SVM), a random forest, a decision tree, or the like, may be used.

As illustrated in FIG. 19A, in a case where the data at the time of the steady state of a large number of patients and a steady state label are prepared as training data and the data at the time of the steady state of the training data is input to the classifier 90, the classifier 90 performs learning so that output data to be output by the classifier 90 matches the steady state label as a teacher label. The training data can be classified for each patient background group.

In addition, as illustrated in FIG. 19B, data at the time of exacerbation of a large number of patients and an exacerbation label are prepared as training data, and in a case where the data at the time of exacerbation of the training data is input to the classifier 90, the classifier 90 performs learning so that output data to be output by the classifier 90 matches the exacerbation label as a teacher label. The training data can be classified for each patient background group. Note that the time-series data of the cluster labels described in FIG. 18 may be input as the training input data.

As described above, the training data classified for each patient background group includes patient data at the time of the steady state and patient data at the time of exacerbation of a large number of patients, and the steady state label indicating the patient data at the time of the steady state and the exacerbation label indicating the patient data at the time of exacerbation. The control unit 60 can generate a classification model to classify the patient as a steady state in a case where the patient data at the time of the steady state of the patient is input and to classify the patient as exacerbation in a case where the patient data at the time of exacerbation of the patient is input.

As illustrated in FIG. 19C, at the time of prediction of exacerbation, data at the time of evaluation of the target patient is input to the classifier 90, and the exacerbation score can be calculated on the basis of accuracy (probability) of the steady state label or the exacerbation label to be output by the classifier 90. The output of the classifier 90 may be only the exacerbation label. For example, the accuracy of the exacerbation label can be set to a range from 0 to 1, and if the accuracy is 0.5 or more, it can be determined as exacerbation, and the exacerbation score can be set to 0.5. In addition, if the accuracy is less than 0.5, it can be determined as the steady state. The exacerbation score may be a continuous value such as a range from 0 to 1 or may be a binary value such as 0 or 1. Learning and execution of the classifier can be performed separately for each patient background group.

As described above, the prediction model includes a classification model (classifier) that classifies the target patient as the steady state or exacerbation in a case where patient data of the target patient is input. The control unit 60 can input patient data at the time of evaluation of the target patient to the classification model to predict exacerbation of the target patient.

FIG. 20 is a view illustrating an example of a causal network model. FIG. 20 illustrates a Bayesian network as an example of the causal network model. The Bayesian network is one of probability models having a graph structure and is a probability model in which a qualitative dependence relationship between a plurality of random variables is represented by a graph structure and a quantitative relationship between individual variables is represented by a conditional probability. In other words, the probability model is defined by a set of random variables, a graph structure representing a dependence relationship between the random variables, and a conditional probability. The random variables constituting the graph are referred to as nodes, and a stochastic dependence relationship between the nodes is connected by an arrow called an arc. The node indicating a cause is X1, and the relationship of a node X2 as a result of X1 is expressed as X1→X2.

As illustrated in FIG. 20, in the Bayesian network of the present embodiment, the biological data, the feature amounts, the medical information, and objective variables are set as nodes. In the example of FIG. 20, the objective variable is "deterioration in cardiac function", which is a node corresponding to and causing exacerbation. Each node of the biological data, the feature amounts, and the medical information corresponds to a result for the cause. The biological data is measurable random variables, the feature amounts are random variables that can be estimated on the basis of the measurable biological data, and the medical information is random variables of information as a result of the cause. The graph structure as illustrated in FIG. 20 can be manually constructed, for example, from a medical viewpoint of a skilled doctor, an expert, or the like, or from specialized knowledge such as guidelines regarding organ failure. The network structure may be searched using data related to past organ failure (for example, data of all patients, data for each patient background group, or the like). Note that an example of the configuration of the Bayesian network (node, arc) is an example and is not limited to the configuration of FIG. 20.

Probabilistic inference by the Bayesian network is performed in the following procedures: (1) measured data is set in a node; (2) a prior probability distribution is given to a node having no measurement value; and (3) a posterior probability of an objective variable is obtained.

FIG. 21 is an example of a data table for giving the biological data and the feature amount to the node. The data table is configured in time series as . . . , (n−1)-th, n-th, . . . . Each data table has time-series data with the window width W and is a set of vectors obtained by sliding the time-series data by the number of slides N. The (n−1)-th table data has a statistic S(n−1), and the n-th table data has a statistic Sn. The statistic includes, for example, a median value, a standard deviation, and the like. The n-th table data has a difference $\Delta S(n)=S(n)-S(n-1)$ between the n-th statistic S(n−1) and the (n−1)-th statistic S(n−1) for each window width. The same applies to other data tables. As the statistic of the feature amount, the instantaneous feature amount illustrated in FIG. 3 can be used. By giving the biological data and the feature amount illustrated in FIG. 21 to the node of the Bayesian network illustrated in FIG. 20, it is possible to set the measured data in the node and give the prior probability distribution to the node having no measurement value. Note that, in a case where the medical information can be given to the node, the medical information may be input to the table data.

Next, the posterior probability of each node can be set by giving patient data of all patients with organ failure (for example, heart failure, or the like) or patient data for each patient background group to the node of the Bayesian network. Note that, in a case where the medical information is available, a degree of progression of the disease, a change in the examination data, a compliance level of the drug, and the like, may be input.

As described above, the training data classified for each patient background group includes transition data of the statistic of the patient data within a predetermined section. The control unit 60 generates a network structure (provides prior probability distribution) including patient data nodes (which may include, for example, nodes representing biological data and feature amounts, and nodes representing medical information) and exacerbation nodes on the basis of the transition data. The control unit 60 can input patient data to the patient data nodes of the generated network structure and set a probability of each node to generate the Bayesian network.

Also, as described above, the prediction model includes the Bayesian network including patient data nodes and exacerbation nodes. The control unit 60 may input patient data at the time of evaluation of the target patient to the patient data nodes of the Bayesian network to predict exacerbation of the target patient.

The domain knowledge by segmentation may be utilized for prediction of exacerbation. Specifically, (1) input data such as biological data is classified for each characteristic distribution using unsupervised learning (for example, segmentation, or the like). (2) Next, the doctor, or the like, refers to the segmentation and labels whether or not the section is a section with an exacerbation symptom. (3) Next, it is determined whether or not there is an exacerbation symptom by classifying which segmentation described above that the patient data of the target patient is close to. (4) Alternatively, which segmentation described above that the patient data of the target patient is close to is automatically determined by a probability density ratio, or the like. The above-mentioned steps (1), (2), and (3), or steps (1), (2), and (4) make it possible to utilize the domain knowledge for determination of an exacerbation symptom.

Next, a method of calculating the exacerbation score will be described.

The exacerbation score calculation function 67 (control unit 60) calculates and outputs the exacerbation score on the basis of exacerbation prediction predicted by the prediction model. Note that the prediction model may directly calculate and output the exacerbation score. The exacerbation score may be an exacerbation score (whether exacerbation or the steady state, a numerical value of exacerbation, and the like) to be output by the prediction model or may be accuracy (probability) of the exacerbation to be output by the prediction model.

A threshold may be set for the exacerbation score to be output by the prediction model (may be set for each prediction model), and exacerbation may be determined in a case where the exacerbation score exceeds the threshold. In addition, a history of exacerbation prediction results of the prediction model may be collected, and the threshold may be adjusted according to the collected exacerbation prediction results. For example, in a case where there is a low ratio of the target patient being not actually exacerbated although a relatively large number of cases are determined as the state of the target patient being "exacerbated" from the exacerbation prediction results of the prediction model, it is possible to adjust the threshold by increasing the threshold to reduce the number of cases in which the state of the target patient is erroneously determined as "exacerbation". In addition, the threshold may be set or adjusted from a medical viewpoint such as the domain knowledge.

FIG. 22 is a view illustrating an example of calculation of the exacerbation score. As illustrated in FIG. 22, it is assumed that exacerbation is predicted using three prediction models 1, 2, and 3 for patient data of a certain target patient. It is assumed that the prediction models 1, 2, and 3 are prediction models corresponding to the patient background group to which the target patient belongs. It is assumed that each of the prediction models 1, 2, and 3 outputs the exacerbation predictions 1, 2, and 3. In a case where there are a plurality of prediction models corresponding to the patient background group to which the target patient belongs, the exacerbation score calculation function 67 (the control unit 60) can predict exacerbation of the target patient by applying a predetermined scheme to the prediction results of exacerbation of the plurality of prediction models.

The predetermined scheme may be, for example, averaging the prediction results of exacerbation of the plurality of prediction models. For example, if the exacerbation predictions 1, 2, and 3 of the prediction models 1, 2, and 3 are set as exacerbation scores of 0.6, 0.7, and 0.8, the average value is 0.7, and thus the final exacerbation score is 0.7. In addition, in a case where the exacerbation predictions 1, 2, and 3 of the prediction models 1, 2, and 3 are the steady state, exacerbation, and exacerbation, a majority decision (i.e., greater number) of the exacerbation predictions of the respective prediction models may be used as the final exacerbation score. In this case, two prediction models output exacerbation and one prediction model outputs the steady state, and thus, the final exacerbation score becomes exacerbation by majority decision.

Furthermore, the exacerbation predictions of the prediction models for each patient background group and the history of correct answers for each exacerbation prediction of the prediction models may be collected, and a prediction model with a high correct answer rate may be preferentially used, and use of a prediction model with a low correct answer rate may be stopped or re-learning may be performed. Next, a method of providing exacerbation information will be described.

The exacerbation information provision function 68 (control unit 60) has a function of providing exacerbation information such as exacerbation prediction by the prediction model execution function 66 or an exacerbation score by the exacerbation score calculation function 67 so that, for example, a doctor, or the like, can refer to the exacerbation information. The exacerbation information provision function 68 (control unit 60) can display the exacerbation information on the display unit 30 or output the exacerbation information to an external device (such as a display device). Hereinafter, an example of provision of the exacerbation information will be described.

FIG. 23 is a view illustrating a first example of provision of the exacerbation information. FIG. 23 indicates the exacerbation score (for example, 0 to 1) on the vertical axis and indicates time on the horizontal axis. FIG. 23 illustrates transition of a change in the exacerbation score calculated from actual patient data of organ failure. The exacerbation score has been on an increasing trend from around the middle of July, and an exacerbation event of organ failure has actually occurred around the middle of August. In other words, it can be seen that the exacerbation score increases from before the occurrence of the exacerbation event (in the example of FIG. 23, about one month ago).

As described above, according to the exacerbation prediction device 100 of the present embodiment, it is possible to predict exacerbation of the organ failure before the occurrence of the exacerbation event and to improve accuracy of prediction of the exacerbation of the patient with organ failure.

FIG. 24 is a view illustrating a second example of provision of the exacerbation information. FIG. 24 indicates the exacerbation score (for example, 0 to 1) on the vertical axis and indicates time on the horizontal axis. In FIG. 24, a threshold for determining whether or not exacerbation occurs is provided on the basis of the exacerbation score, and transition of a change in the exacerbation score calculated from patient data of the target patient is illustrated. As illustrated in FIG. 24, in a case where the exacerbation score starts to increase and the exacerbation score currently exceeds the threshold, it is possible to determine that exacerbation has occurred and make a notification that the target patient is exacerbated. The notification of exacerbation may be displayed on the display unit 30 or may be output to an external device. As a result, the doctor can grasp in advance that an exacerbation event may occur in the target patient in the near future and can perform appropriate treatment and medication at an early stage.

FIG. 25 is a view illustrating a third example of provision of exacerbation information. An exacerbation information provision screen of FIG. 25 has an area for displaying the latest distribution of the biological data or feature amounts of the target patient, an area for displaying the distribution of the biological data or feature amounts for each patient background group, an area for geometrically displaying which patient background group the target patient belongs to, and an area for receiving operation of changing the patient background group to which the target patient belongs. In the example of FIG. 25, the distribution of the biological data or the feature amounts of each of the three patient background groups is displayed, and three areas indicating the patient background groups are illustrated by closed curves, and which of the three patient background groups the data of the target patient (in FIG. 25, the "star" represents the target patient) belongs to is geometrically represented. In addition, FIG. 25 shows how an operation is performed to change the patient background group, to which the target patient belongs, from Group 1 to Group 3 by using a drop down list shown in lower right in FIG. 25.

As described above, the exacerbation information provision function 68 (control unit 60) can output display information for displaying the distribution information of the biological data or the feature amounts of the target patient and the distribution information of the biological data or the feature amounts of the plurality of classified patient background groups in a comparable manner, which makes it possible to intuitively determine whether or not the distribution information of the biological data or the feature amounts of the target patient is similar to the distribution information of the biological data or the feature amounts of the plurality of patient background groups.

Furthermore, the control unit 60 can receive operation of changing the patient background group to which the target patient belongs, which makes it possible to appropriately set the patient background group to which the target patient belongs.

FIG. 26 is a view illustrating a fourth example of provision of the exacerbation information. An exacerbation information provision screen of FIG. 26 has an area for displaying the latest distribution of the biological data or the feature amounts of the target patient and an area for displaying transition of the exacerbation score predicted by the plurality of prediction models on the basis of the patient data of the target patient. In the example of FIG. 26, the exacerbation prediction results of the prediction models 1, 2, and 3 are displayed. Note that one prediction model may be used. The prediction models 1, 2, and 3 are prediction models corresponding to the patient background group to which the target patient belongs. Furthermore, as illustrated in FIG. 26, the present exacerbation score may be displayed for each prediction model. In the example of FIG. 26, the exacerbation score of the prediction model 1 is 10.02, the exacerbation score of the prediction model 2 is 1.31, and the exacerbation score of the prediction model 3 is 2.89. The transition of the exacerbation score of the prediction model having the largest exacerbation score may be displayed in a display mode (in the example of FIG. 26, surrounded by a frame) that can be compared with the transition of the exacerbation scores of other prediction models.

As described above, in a case where there are a plurality of prediction models corresponding to the patient background group to which the target patient belongs, the exacerbation information provision function 68 (the control unit 60) may output display information for displaying the transition of the prediction results of the exacerbation of the plurality of prediction models in a comparable manner, which makes it possible for the doctor to determine whether or not exacerbation occurs at the present time by checking the results of the plurality of prediction models.

FIG. 27 is a view illustrating a second example of the configuration of the exacerbation prediction system of the present embodiment. The difference from the first example illustrated in FIG. 1 is that the exacerbation prediction device 100 includes a storage unit 69 inside a control unit 60 instead of the storage unit 70, that the server 150 (external device, cloud, or the like) is provided separately from the exacerbation prediction device 100, that the server 150 includes a patient background group/prediction model table 151, a patient background group construction function 152, and a prediction model learning function 153, and that the exacerbation prediction device 100 does not include the patient background group construction function 62 and the prediction model learning function 64.

The storage unit 69 has a configuration similar to that of the storage unit 70. The patient background group/prediction model table 151 is similar to the patient background group/prediction model table illustrated in FIG. 11. In addition, the patient background group construction function 152 and the prediction model learning function 153 have functions similar to those of the patient background group construction function 62 and the prediction model learning function 64, respectively.

The server 150 can generate the patient background group/prediction model table 151 by executing the patient background group construction function 152 and the prediction model learning function 153. The exacerbation prediction device 100 can acquire the patient background group/prediction model table 151 from the server 150 and store it in the storage unit 69.

FIG. 28 is a view illustrating a second example of the prediction model execution processing. The processing illustrated in FIG. 28 is based on the second example of the configuration of the exacerbation prediction system illustrated in FIG. 27. The control unit 60 acquires biological data of a target patient to be evaluated for exacerbation (S51)

and processes the acquired biological data to specify feature amounts (S52). The control unit 60 acquires medical information including patient attribute information, disease information, diagnosis information, treatment information, and medication information of the target patient (S53). The medical information may include domain knowledge.

The control unit 60 (the patient background group selection function 63, the patient background selection unit) selects a patient background group to which the target patient to be evaluated for exacerbation belongs from a plurality of patient background groups in the patient background group/prediction model table 151 stored in the storage unit 69 (S54). The control unit 60 (the prediction model selection function 65, the prediction model calling unit) calls one or more prediction models corresponding to the patient background group to which the target patient belongs, from one or more prediction models in the patient background group/prediction model table 151 stored in the storage unit 69 (S55).

The control unit 60 (the prediction model execution function 66 and the exacerbation score calculation function 67) inputs at least part of the patient data including the biological data, the feature amounts, and the medical information of the target patient to the called prediction model to predict exacerbation of the target patient (S56) and ends the processing.

As described above, the control unit 60 may include a patient data acquisition unit that acquires patient data of a target patient to be evaluated for exacerbation, a storage unit that stores a plurality of patient background groups classified by patient data of a plurality of patients collected in advance and one or more prediction models prepared in advance for each of the plurality of patient background groups, a patient background group selection unit that selects a patient background group to which the target patient to be evaluated for exacerbation belongs from the plurality of patient background groups stored in the storage unit, a prediction model calling unit that calls one or more prediction models corresponding to the patient background group to which the target patient belongs from the one or more prediction models stored in the storage unit, and a prediction unit that inputs at least part of the acquired patient data of the target patient to the called prediction model to predict exacerbation of the target patient.

Note that the patient background group construction function 152 and the prediction model learning function 153 may be removed from the server 150, the patient background group construction function 152 and the prediction model learning function 153 may be provided in a device different from the server 150, the device may execute the patient background group construction function 152 and the prediction model learning function 153 to generate the patient background group/prediction model table 151, and the server 150 may acquire the patient background group/prediction model table 151 from the device and simply store only the patient background group/prediction model table 151.

The detailed description above describes an exacerbation prediction device, a computer program, an exacerbation prediction method, a prediction model generation method, and a prediction model generation device. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. An exacerbation prediction system for heart failure comprising:
   a wearable device configured to be worn on a target patient to be evaluated for exacerbation of heart failure, the wearable device comprising:
      a sensor configured to measure biological data of the target patient; and
      a communication unit configured to transmit the measured biological data;
   a data collection device configured to:
      receive the biological data from the wearable device; and
      accumulate the biological data;
   an exacerbation prediction device comprising a control unit, the control unit configured to:
      acquire the accumulated biological data of the target patient from the data collection device;
      specify feature amounts related to heart failure obtained by processing the acquired accumulated biological data;
      input the acquired accumulated biological data and the feature amounts to a prediction model for calculating an exacerbation score for heart failure of the target patient, wherein the exacerbation score is a continuous value representing a degree of exacerbation of heart failure;
      calculate the exacerbation score of the target patient;
      output, to an external display device, a graph showing a time-series transition of the exacerbation score;
      determine that the target patient is in exacerbation when the exacerbation score exceeds a predetermined threshold; and
      output, on the graph displayed on the external display device, a notification indicating that the target patient is in exacerbation of heart failure when the exacerbation score exceeds the predetermined threshold.

2. The exacerbation prediction system according to claim 1,
   wherein the data collection device is further configured to:
      receive medical information of the target patient from a medical information system, the medical information depending on at least one of patient attribute information, disease information, diagnosis information, treatment information, or medication information of the target patient; and
      accumulate the medical information for each target patient; and
   wherein the control unit is configured to:
      receive the accumulated medical information from the data collection device; and
      input the medical information to the prediction model with the acquired accumulated biological data and the feature amounts to calculate the exacerbation score of the target patient.

3. The exacerbation prediction system according to claim 1, wherein the control unit is configured to:
   select a patient background group to which the target patient belongs, from a plurality of patient background groups classified in advance on a basis of the biological data and the feature amounts;
   select one or more prediction models corresponding to the patient background group to which the target patient belongs, from one or more prediction models prepared in advance for each of the plurality of patient background groups; and input the acquired accumulated biological data and the feature amounts to the selected prediction model to calculate the exacerbation score of the target patient.

4. The exacerbation prediction device according to claim 1, wherein the temporal change feature amount includes at least one of a blood pressure change index, heart rate variability, pulse variability, a respiration complexity, or a complexity of the heart rate variability.

5. The exacerbation prediction system according to claim 1, wherein the temporal change feature amount includes at least one of changes in periodicity of a residual component and a trend component separated from tendency target information including at least one of the biological data or the feature amounts obtained by processing the biological data, and a seasonal periodic component separated from the tendency target information.

6. The exacerbation prediction system according to claim 1, wherein the temporal change feature amount includes probability density of entropy of at least one of the biological data or the feature amounts obtained by processing the biological data.

7. The exacerbation prediction system according to claim 1, wherein the instantaneous feature amount includes at least one of a blood pressure index, an edema index, an extracellular water index, a stroke volume, sympathetic nerve information, parasympathetic nerve information, an activity amount index, a sleep index.

8. The exacerbation prediction system according to claim 1, wherein the wearable device includes an impedance measurement function and a photoelectric plethysmography function; and wherein the acquired accumulated biological data includes an extracellular water resistance value to be measured by the impedance measurement function and a pulse wave or a pulse rate to be measured by the photoelectric plethysmography function.

9. The exacerbation prediction system according to claim 8, wherein the wearable device further includes an acceleration measurement function; and wherein the acquired accumulated biological data further includes an activity amount to be measured by the acceleration measurement function.

10. The exacerbation prediction system according to claim 1, wherein the wearable device includes a data processing function, the data processing function configured to attach an identifier of the target patient to the measured biological data and output the acquired accumulated biological data to the communication unit.

11. The exacerbation prediction system according to claim 1, wherein the wearable device includes an impedance measurement function, a photoelectric plethysmography function, and an acceleration measurement function;

wherein the acquired accumulated biological data includes an extracellular water resistance value to be measured by the impedance measurement function and a pulse wave or a pulse rate to be measured by the photoelectric plethysmography function;

wherein the temporal change feature amount includes pulse variability calculated from the pulse wave or the pulse rate; and wherein the instantaneous feature amount includes:

extracellular water index calculated based on the extracellular water resistance value; and an activity amount index including a value counted each time a value of an acceleration sensor of the acceleration measurement function becomes greater than or equal to a predetermined value.

* * * * *